US012254710B2

(12) United States Patent
Chennubhotla et al.

(10) Patent No.: US 12,254,710 B2
(45) Date of Patent: *Mar. 18, 2025

(54) PREDICTING CANCER RECURRENCE FROM SPATIAL MULTI-PARAMETER CELLULAR AND SUBCELLULAR IMAGING DATA

(71) Applicant: UNIVERSITY OF PITTSBURGH-OF THE COMMONWEALTH SYSTEM OF HIGHER EDUCATION, Pittsburgh, PA (US)

(72) Inventors: Srinivas C. Chennubhotla, Pittsburgh, PA (US); Douglass L. Taylor, Pittsburgh, PA (US); Shikhar Uttam Fnu, Pittsburgh, PA (US)

(73) Assignee: University of Pittsburgh—Of The Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/493,740

(22) Filed: Oct. 24, 2023

(65) Prior Publication Data

US 2024/0062564 A1 Feb. 22, 2024

Related U.S. Application Data

(63) Continuation of application No. 17/056,080, filed as application No. PCT/US2019/033662 on May 23, 2019, now Pat. No. 11,836,998.
(Continued)

(51) Int. Cl.
*G06V 20/69* (2022.01)
*G06F 18/21* (2023.01)
(Continued)

(52) U.S. Cl.
CPC .......... *G06V 20/698* (2022.01); *G06F 18/211* (2023.01); *G06F 18/217* (2023.01);
(Continued)

(58) Field of Classification Search
CPC ...... G06V 20/698; G06V 10/26; G06V 10/50; G06V 10/771; G06V 10/776;
(Continued)

(56) References Cited

U.S. PATENT DOCUMENTS

2010/0177950 A1 7/2010 Donovan et al.
2012/0219206 A1 8/2012 Janowczyk et al.
(Continued)

FOREIGN PATENT DOCUMENTS

JP 2014-519818 A 8/2014
JP 2017-516992 A 6/2017
(Continued)

OTHER PUBLICATIONS

Rothberg et al. "Construction and analysis of multi-parameter prognostic models for melanoma outcome." In: Methods Mel Biol. 2014;, (online) (retrieved on Jul. 18, 2019 (Jul. 18, 2019)) Retrieved from the Internet <URL: https://www.ncbi.nlm.nih.gov/pmc/articles/PMC3912557/>, entire document, especially Abstract; p. 1-5, 11-12, 17-19, 22-24.
(Continued)

*Primary Examiner* — Qian Yang
(74) *Attorney, Agent, or Firm* — Philip E. Levy; Cherin & Mellott, LLC

(57) ABSTRACT

A method of predicting cancer recurrence risk for an individual includes receiving patient spatial multi-parameter cellular and sub-cellular imaging data for a tumor of the individual, and analyzing the patient spatial multi-parameter cellular and sub-cellular imaging data using a prognostic model for predicting cancer recurrence risk to determine a
(Continued)

predicted cancer recurrence risk for the individual, wherein the joint prognostic model is based on spatial correlation statistics among features derived for a plurality of intra-tumor spatial domains from spatial multi-parameter cellular and sub-cellular imaging data obtained from a plurality of cancer patients.

22 Claims, 24 Drawing Sheets

Related U.S. Application Data

(60) Provisional application No. 62/675,832, filed on May 24, 2018.

(51) Int. Cl.
| | | |
|---|---|---|
| *G06F 18/211* | (2023.01) | |
| *G06V 10/26* | (2022.01) | |
| *G06V 10/50* | (2022.01) | |
| *G06V 10/771* | (2022.01) | |
| *G06V 10/776* | (2022.01) | |
| *G16H 30/40* | (2018.01) | |
| *G16H 50/20* | (2018.01) | |
| *G06N 20/00* | (2019.01) | |

(52) U.S. Cl.
CPC .............. *G06V 10/26* (2022.01); *G06V 10/50* (2022.01); *G06V 10/771* (2022.01); *G06V 10/776* (2022.01); *G16H 30/40* (2018.01); *G16H 50/20* (2018.01); *G06N 20/00* (2019.01); *G06V 2201/03* (2022.01)

(58) Field of Classification Search
CPC . G06V 2201/03; G06F 18/211; G06F 18/217; G16H 30/40; G16H 50/20; G06N 20/00; Y02A 90/10
See application file for complete search history.

(56) References Cited

U.S. PATENT DOCUMENTS

| | | |
|---|---|---|
| 2013/0230230 A1 | 9/2013 | Ajemba et al. |
| 2014/0127708 A1 | 5/2014 | Muraca |
| 2015/0133321 A1 | 5/2015 | O'Shannessy |
| 2016/0003829 A1 | 1/2016 | Bhaumik |
| 2016/0333421 A1 | 11/2016 | Boutros et al. |
| 2017/0091937 A1 | 3/2017 | Barnes |
| 2017/0270420 A1 | 9/2017 | Harder et al. |
| 2017/0365053 A1 | 12/2017 | Yuan |

FOREIGN PATENT DOCUMENTS

| | | |
|---|---|---|
| JP | 2018-504674 A | 2/2018 |
| JP | 2019-534451 A | 11/2019 |
| WO | 2012154722 A1 | 11/2012 |
| WO | 2013052480 A1 | 4/2013 |
| WO | 2015040990 A1 | 3/2015 |

OTHER PUBLICATIONS

Galon, Jerome et al., "Type, Density, and Location of Immune Cells Within Human Colorectal Tumors Predict Clinical Outcome", vol. 313 Science, www.sciencemag.org, Sep. 29, 2006, 8 pp. (1960-1964).
Galon, Jerome et al., Journal of Pathology, J Pathol 2014; 232: Published online in Wiley Online Library (wileyonlinelibrary.com) DOI: 10.1002/path.4287, 11 pp. (199-209).
Au, Qingyan et al., "Abstract 5135: Detection of IFNγ induced PDL1 expression by combined in situ RNA analysis and proteinprofiling from a single FFPE slide", Proceedings: AACR 107th Annual Meeting 2016; Apr. 16-20, 2016; New Orleans, LA, https://cancerres-aacrjournals-org.pitt.idm.oclc.org/content/76/14_Supplement/5135, Published Jul. 2016, 4 pp.
Steven J. Potts et al., "Evaluating tumor heterogeneity in immunohistochemistry-stained breast cancer tissue", www.laboratoryinvestigation.org | Laboratory Investigation | vol. 92 Sep. 2012, pp. 1342-1357.
Daniel M. Spagnolo et al., "Pointwise mutual information quantifies intratumor heterogeneity in tissue sections labeled with multiple fluorescent biomarkers", @ 2016 Journal of Pathology Informatics, http://www.jpathinformatics.org on Saturday, Jan. 28, 2017, IP: 150.212.235.111, 18 pp.
Albert Gough et al., "Biologically Relevant Heterogeneity: Metrics and Practical Insights", SLAS Discovery 2017, vol. 22(3) 213-237 @ 2017 Society for Laboratory Automation and Screening DOI: 10.1177/2472555216682725 journals.sagepub.com/home/jbx, 25 pp.
Akif Burak Tosun et al. "Histological Detection of High-Risk Benign Breast Lesions from Whole Slide Images", Dept. of Computational and Systems Biology, Univ. of Pittsburgh, Pittsburgh, USA, Dept. of Pathology, Magee Womens Hospital of UPMC, Pittsburgh, USA, Drug Discovery Institute, Univ. of Pittsburgh, Pittsburgh, USA, 8 pp.
Luong Nguyen et al., "Spatial Statistics for Segmenting Histological Structures in H&E Stained Tissue Images", IEEE Transactions on Medical Imaging, vol. 36, No. 7, Jul. 2017, http://www.ieee.org/publications_standards/publications/rights/index.html, pp. 1522-1532.
L. Nguyen et al., "Architectural Patterns for Differential Diagnosis of Proliferative Breast Lesions From Histopathological Images". Department of Computational and Systems Biology, Drug Discovery Institute, Magee Womens Hospital of UPMC and Department of Pathology, University of Pittsburgh, 5 pp.
C. Chennubhotla et al., "An Assessment of Imaging Informatics for Precision Medicine in Cancer", @ 2017 IMIA and Schattauer GmbH, IMIA Yearbook of Medical Informatics 2017, 4 pp. (110-119).
Albert Gough et al., "High Content Analysis With Cellular and Tissue Systems Biology: a Bridge Between Cancer Cell Biology and Tissue-Based Diagnostics", Chapter for "The Molecular Basis of Cancer", 4th Edition (In Press), pp. 1-81.
Daniel M. Spagnolo et al., "Platform for Quantitative Evaluation of Spatial Intratumoral Heterogeneity in Multiplexed Fluorescence Images", Focus on Computer Resources, Downloaded from cancerres.aacrjournals.org on May 10, 2018. @ 2017 American Association for Cancer Research, Cancer Res; 77(21) Nov. 1, 2017, pp. e71-e74 (5 pp.).
Alexandre Calon et al "Stromal gene expression defines poor-prognosis subtypes in colorectal cancer", vol. 47 | No. 4 | Apr. 2015 Nature Genetics, pp. 320-332.
Felipe De Sousa E Melo et al., "Poor-prognosis colon cancer is defined by a molecularly distinct subtype and develops from serrated precursor lesions", vol. 19 | No. 5 | May 2013 Nature Medicine, pp. 614-621.
Michael J. Gerdes et al. "Highly multiplexed single-cell analysis of formalinfixed, paraffin-embedded cancer tissue", www.pnas.org/cgi/doi/10.1073/pnas, 11982-11987 | PNAS | Jul. 16, 2013 | vol. 110 | No. 29, pp. 1-6.
Robin K. Kelley, MD et al. "Biomarker Use in Colorectal Cancer Therapy", NIH Public Access, J Natl Compr Canc Netw. Author manuscript; available in PMC Jul. 1, 2013. Published in final edited form as: J Natl Compr Canc Netw. Nov. 2011 ; 9(11): 1293-1302.
Richard D. Kennedy et al. "Development and Independent Validation of a Prognostic Assay for Stage II Colon Cancer Using Formalin-Fixed Paraffin-Embedded Tissue", Journal of Clinical Oncology, vol. 29, No. 35, Dec. 10, 2011, Downloaded from ascopubs.org by 24.2.127.231 on Dec. 19, 2020 from 024.002.127. 231.
Laetitia Marisa et al. "Gene Expression Classification of Colon Cancer into Molecular Subtypes: Characterization, Validation, and Prognostic Value", Molecular Classification of Colon Cancer, PLOS Medicine | www.plosmedicine.org, May 2013, vol. 10, Issue 5, 13 pp.

(56) References Cited

OTHER PUBLICATIONS

Anguraj Sadanandam et al. "A colorectal cancer classification system that associates cellular phenotype and responses to therapy", Nature Medicine vol. 19 | No. 5 | May 2013, pp. 619-626.
Geetika Srivastava et al. "ProspectiveMulticenter Study of the Impact of Oncotype DX Colon Cancer Assay Results on Treatment Recommendations in Stage II Colon Cancer Patients", TheOncologist 2014;19:492-497 www.TheOncologist.com.
Ramon Salazar et al. "Gene Expression Signature to Improve Prognosis Prediction of Stage II and III Colorectal Cancer", J Clin Oncol 29:17-24. @ 2010 by American Society of Clinical Oncology, Downloaded from ascopubs.org by 24.2.127.231 on Dec. 19, 2020, pp. 17-24.
Written Opinion Issued for PCT/US2019/033662, mailed Aug. 16, 2019.
International Search Report issued in PCT/US2019/033662, mailed Aug. 16, 2019.
Kwak, Jin Tae et al., "Improving prediction of prostate cancer recurrence using chemical imaging", Scientific reports vol. 5 8758. Mar. 4, 2015.
Beck et al., "Systematic Analysis of Breast Cancer Morphology Uncovers Stromal Features Associated with Survival", www.ScienceTranslationalMedicine.org, Nov. 9, 2011, vol. 3, Issue 108, pp. 1-11.
Camp, Robert L., Gina G. Chung, and David L. Rimm. "Automated subcellular localization and quantification of protein expression in tissue microarrays." (2002): 1323-1328. (Year: 2002).
Sushil Mittal, David Madigan, Randall S. Burd, Marc A. Suchard, High-dimensional, massive sample-size Cox proportional hazards regression for survival analysis, Biostatistics, vol. 15, Issue 2, Apr. 2014, pp. 207-221 (Year: 2014).
Tosun, A. B. et al. (2017). Histological Detection of High-Risk Benign Breast Lesions from Whole Slide Images. In: Descoteaux, M., Maier-Hein, L., Franz, A., Jannin, P., Collins, D., Duchesne, S. (eds) Medical Image Computing and Computer-Assisted Intervention—MICCAI 2017. MICCAI 2017. Lecture Not (Year: 2017).
Neumeister, Veronique et al. "In situ identification of putative cancer stem cells by multiplexing ALDH1, CD44, and cytokeratin identifies breast cancer patients with poor prognosis." The American journal of pathology vol. 176,5 (2010) (Year: 2010).
Harder, Nathalie et al. "Tissue Phenomics for prognostic biomarker discovery in low- and intermediate-risk prostate cancer." Scientific reports vol. 8, 1 4470. Mar. 13, 2018 (Year: 2018).

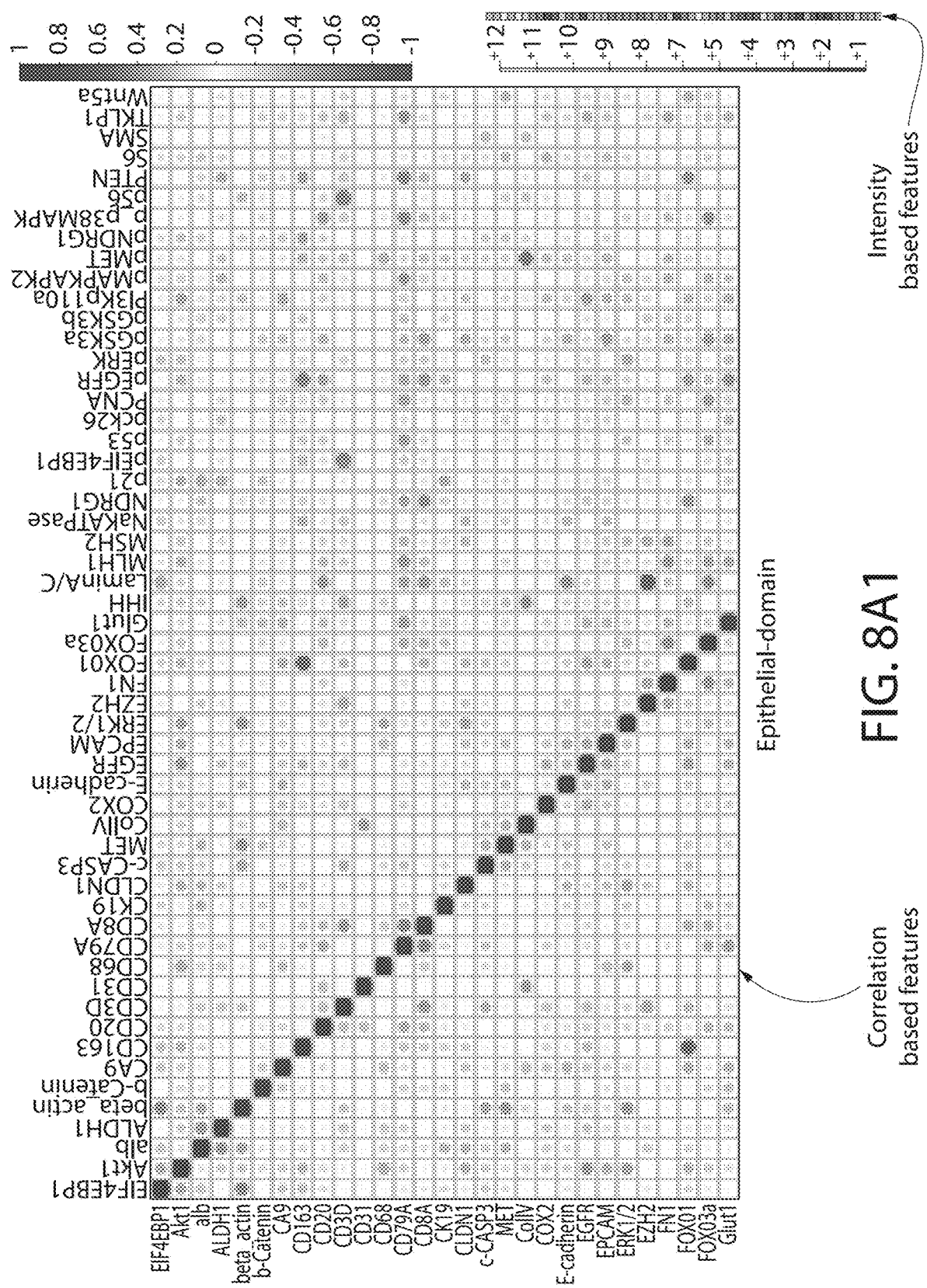
FIG. 8A1

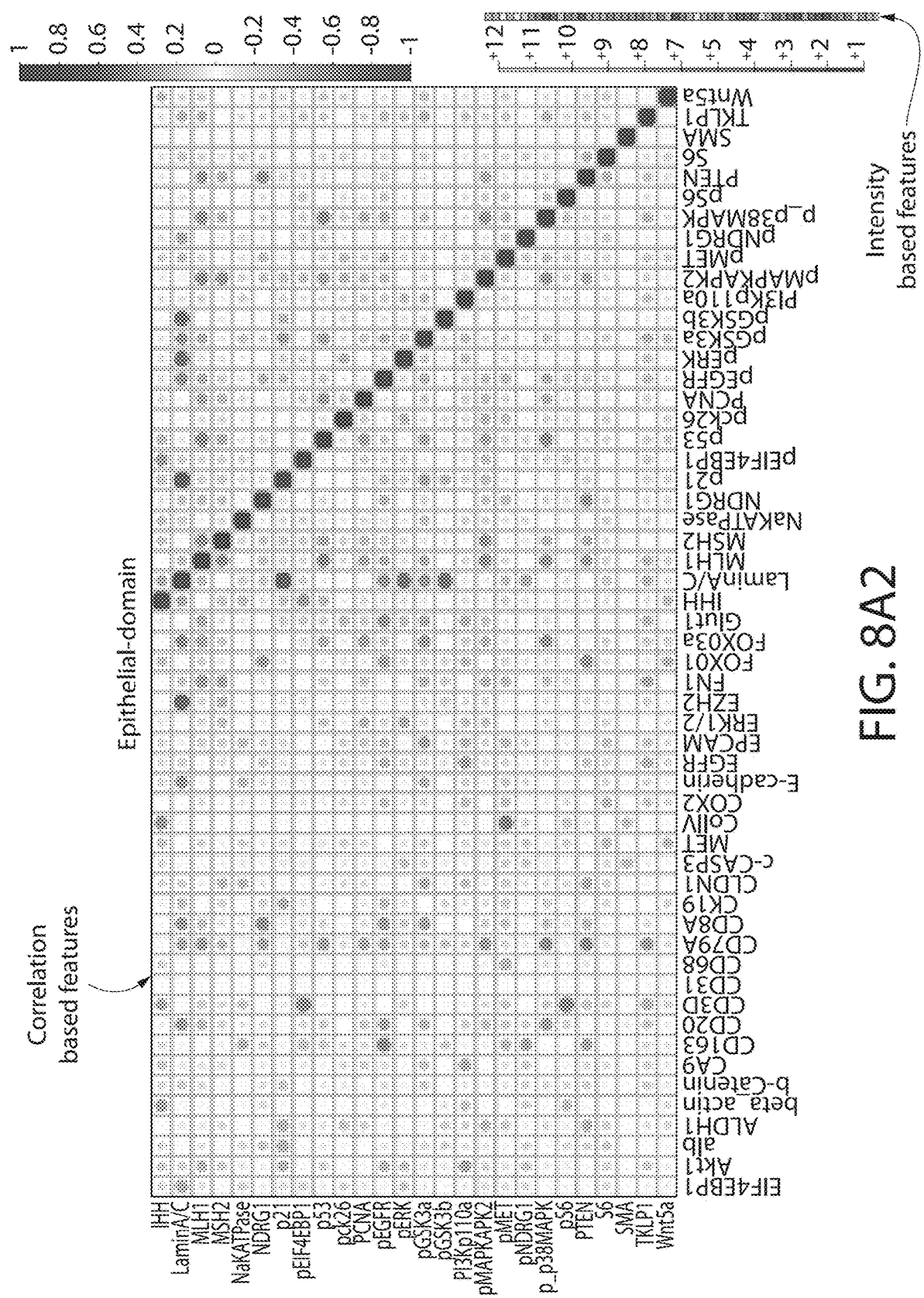
FIG. 8A2

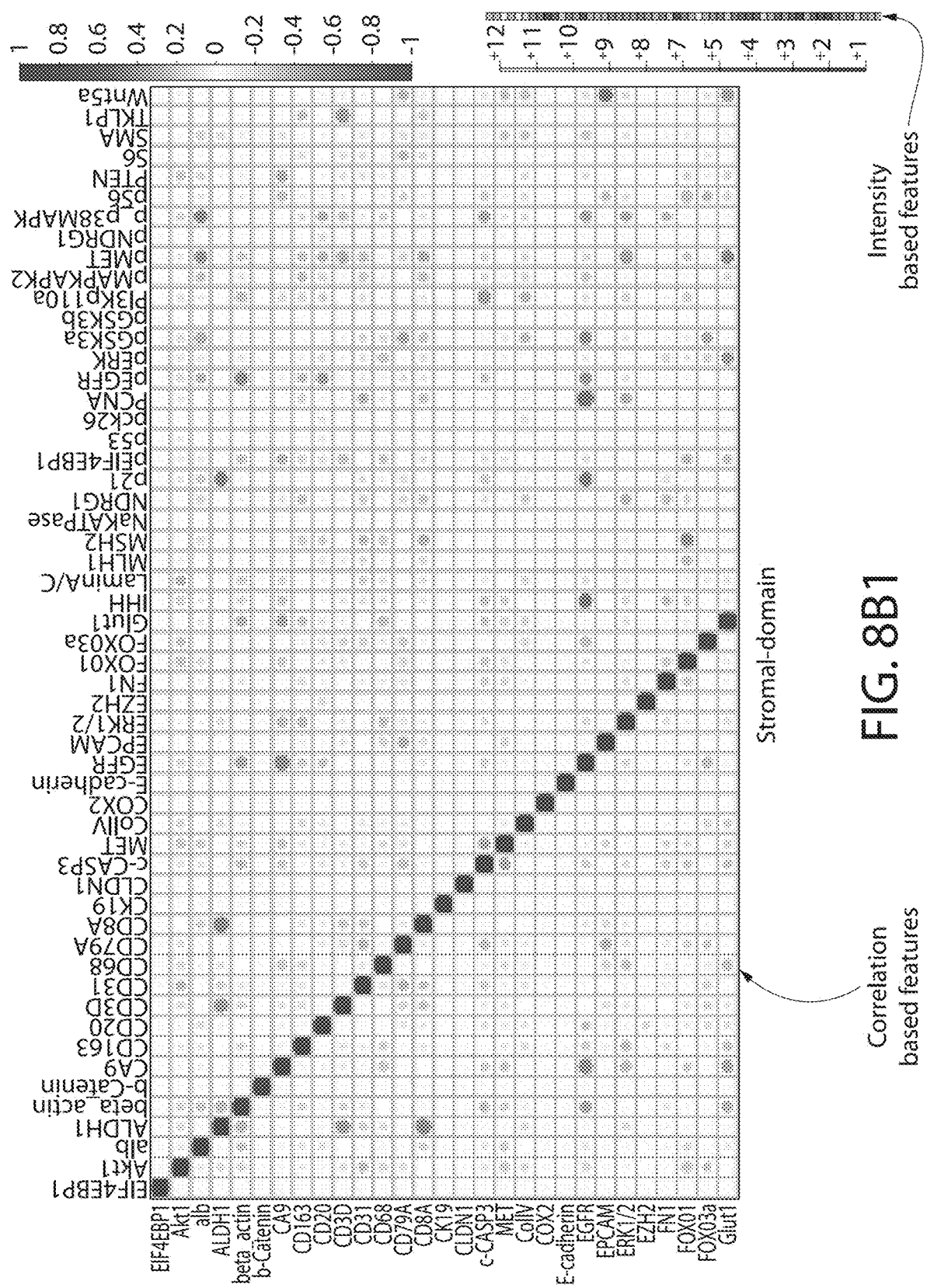
FIG. 8B1

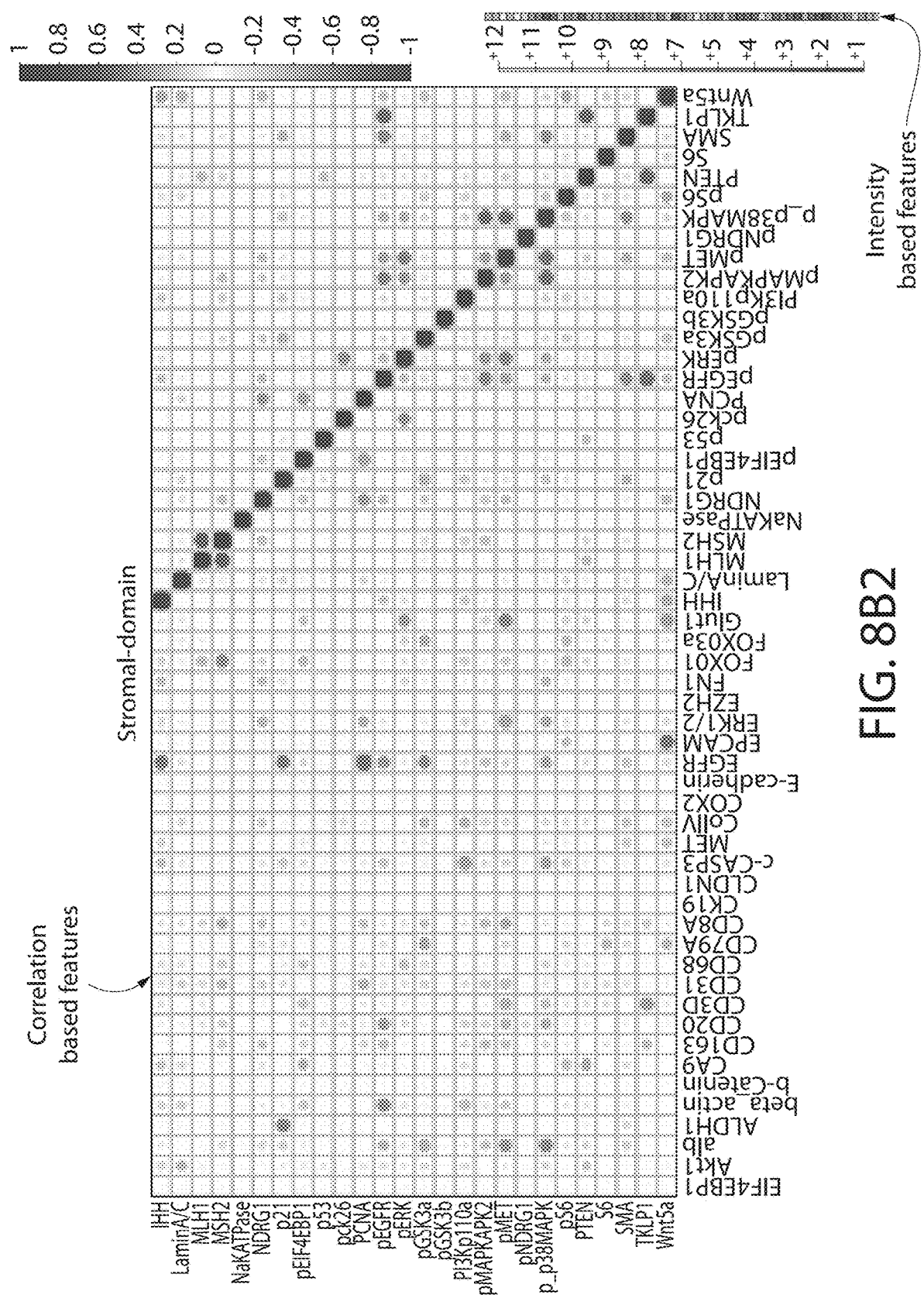
FIG. 8B2

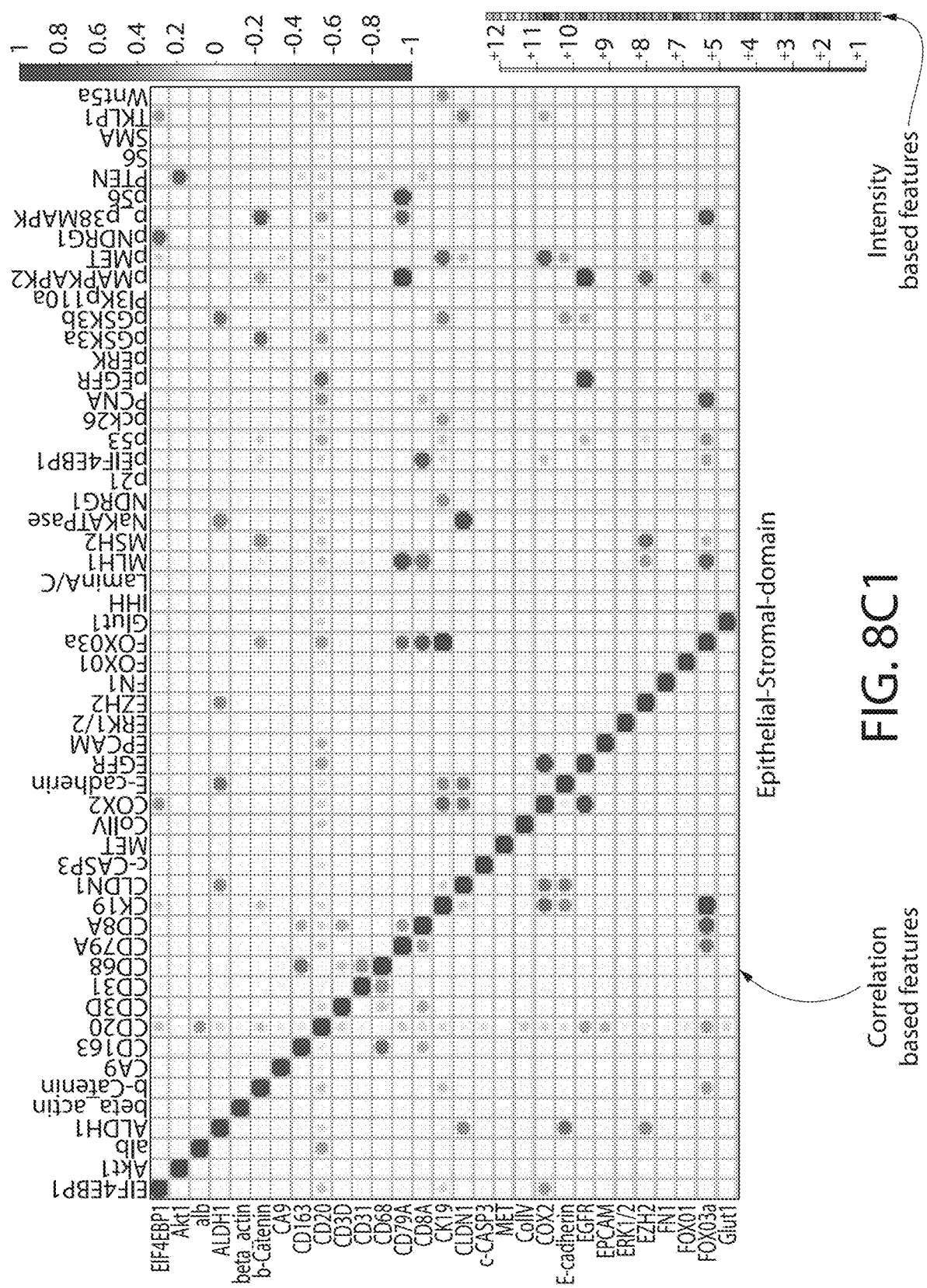
FIG. 8C1

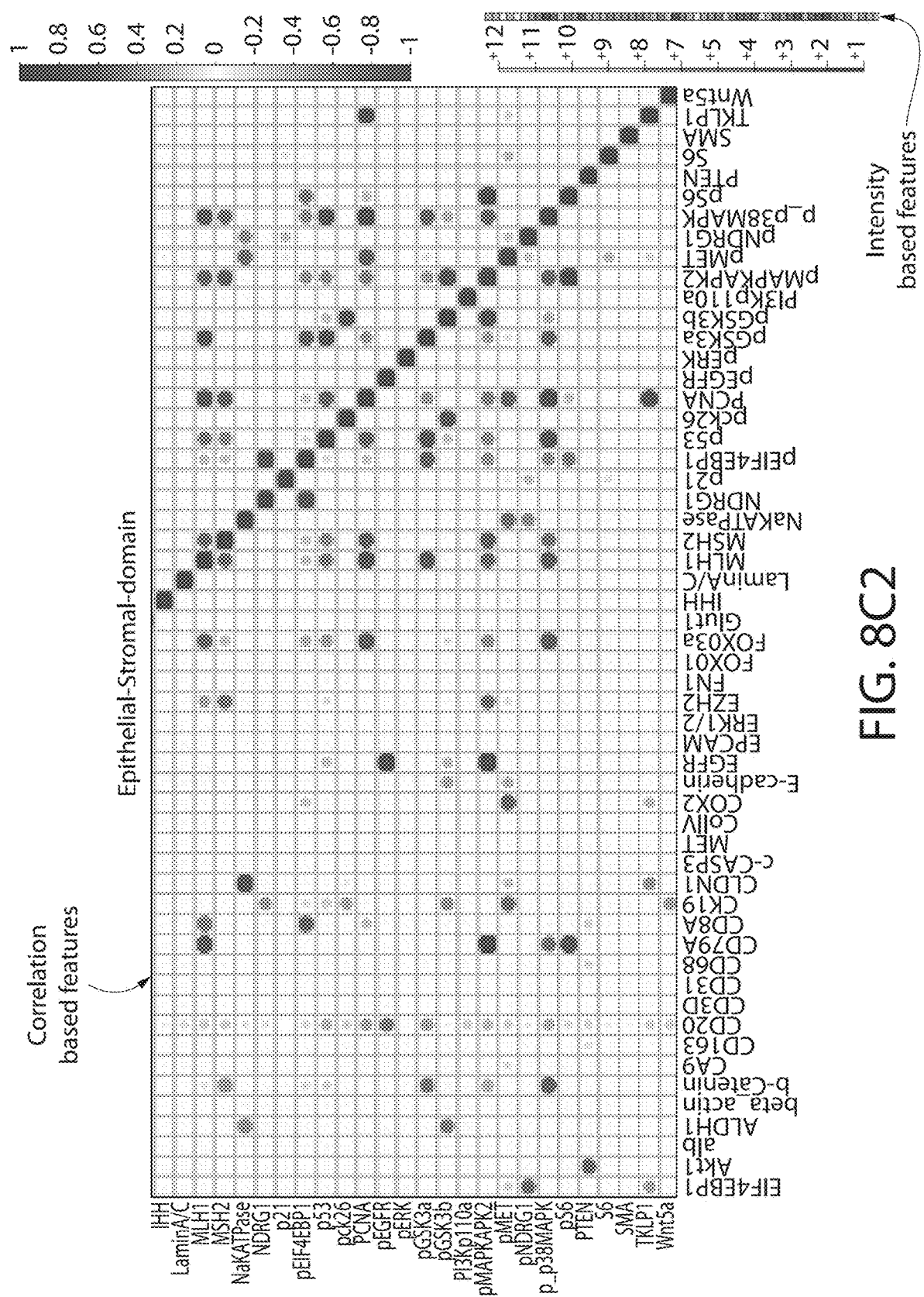
FIG. 8C2

PREDICTING CANCER RECURRENCE FROM SPATIAL MULTI-PARAMETER CELLULAR AND SUBCELLULAR IMAGING DATA

CROSS REFERENCE TO RELATED APPLICATIONS

This application is a continuation application of and claims priority to U.S. patent application Ser. No. 17/056,080, filed on Nov. 17, 2020, entitled "PREDICTING CANCER RECURRENCE FROM SPATIAL MULTI-PARAMETER CELLULAR AND SUBCELLULAR IMAGING DATA, which is a U.S. national stage application under 371 for International Application No. PCT/US2019/033662, filed on May 23, 2019, entitled "PREDICTING CANCER RECURRENCE FROM SPATIAL MULTI-PARAMETER CELLULAR AND SUBCELLULAR IMAGING DATA", which claims priority under 35 U.S.C. § 119(e) from Provisional Patent Application No. 62/675,832, filed on May 24, 2018, entitled "PREDICTING THE RECURRENCE RISK OF CANCER PATIENTS FROM PRIMARY TUMORS WITH MULTIPLEXED IMMUNOFLUORESCENCE BIOMARKERS AND THEIR SPATIAL CORRELATION STATISTICS", the contents of which are incorporated herein by reference.

GOVERNMENT CONTRACT

This invention was made with government support under grant #CA204826 awarded by the National Institutes of Health (NIH). The government has certain rights in the invention.

BACKGROUND OF THE INVENTION

Field of the Invention

The disclosed concept pertains to digital pathology, and, in particular, to systems and methods for predicting the recurrence risk for cancer patients from spatial multi-parameter cellular and sub-cellular imaging data from primary tumors and spatial correlation statistics obtained therefrom by identifying emergent spatial domain networks associated with recurrence.

Description of the Related Art

Colorectal Cancer (CRC) is the second most common type of cancer and the third leading cause of cancer-related deaths worldwide. This multi-factorial disease, like other carcinomas, develops and progresses through the selection of epithelial clones with the potential to confer malignant phenotypes in the context of a reciprocally coevolving tumor microenvironment (TME) comprising immune and stromal cells. CRC patients are staged using the well-established tumor-node-metastases (TNM) classification. However, there is significant variability in patient outcomes within each stage. For example, CRC will recur in up to 30% of Stage II patients despite complete tumor resection, no residual tumor burden and no signs of metastasis. In contrast, more advanced CRC has been known to show stability or indeed even to spontaneously regress.

The intrinsic plasticity of the TME underlying this variability in outcome is controlled by a complex network biology emerging from the spatial organization of diverse cell types within the TME and their heterogeneous states of activation. The important role of the TME in CRC progression and recurrence has recently been highlighted by the identification of four consensus molecular subtypes (CMS), functional studies defining the critical role of stromal cells in determining overall survival, and the development of Immunoscore®, which quantifies tumor-infiltrating T-lymphocytes in different regions of the tumor and associates their infiltration with CRC recurrence. However, the TME can be further harnessed to significantly improve CRC prognosis through the identification of biomarkers mechanistically linked to disease progression and the development of novel therapeutic strategies.

SUMMARY OF THE INVENTION

In one embodiment, a method of creating a system for predicting cancer recurrence risk is provided. The method includes receiving spatial multi-parameter cellular and sub-cellular imaging data for a plurality of cancer patients, spatially dissecting spatial multi-parameter cellular and sub-cellular imaging data into a plurality of intra-tumor spatial domains, generating a base feature set for each of the intra-tumor spatial domains, for each of the intra-tumor spatial domains, selecting a subset of features from the base feature set for the intra-tumor spatial domain, for each of the intra-tumor spatial domains, developing and training a spatial domain specific multivariate prognostic model for predicting cancer recurrence risk using the subset of features of the intra-tumor spatial domain, and combining the spatial domain specific multivariate prognostic model of each of the intra-tumor spatial domains into a joint prognostic model for predicting cancer recurrence risk.

In another embodiment, a method of predicting cancer recurrence risk for an individual is provided. The method includes receiving patient spatial multi-parameter cellular and sub-cellular imaging data for a tumor of the individual, and analyzing the patient spatial multi-parameter cellular and sub-cellular imaging data using a joint prognostic model for predicting cancer recurrence risk to determine a predicted cancer recurrence risk for the individual. The joint prognostic model in this embodiment has been previously developed and trained by receiving spatial multi-parameter cellular and sub-cellular imaging data for a plurality of cancer patients, spatially dissecting the spatial multi-parameter cellular and sub-cellular imaging data into a plurality of intra-tumor spatial domains, generating a base feature set for each of the intra-tumor spatial domains, for each of the intra-tumor spatial domains, selecting a subset of features from the base feature set for the intra-tumor spatial domain, for each of the intra-tumor spatial domains, developing and training a spatial domain specific multivariate prognostic model for predicting cancer recurrence risk using the subset of features of the intra-tumor spatial domain, and combining the spatial domain specific multivariate prognostic model of each of the intra-tumor spatial domains into the joint prognostic model for predicting cancer recurrence risk.

In another embodiment, an apparatus for predicting cancer recurrence risk for an individual is provided. The apparatus includes a computer system comprising a processing apparatus implementing a joint prognostic model for predicting cancer recurrence risk, wherein the processing apparatus is structured and configured to receive patient spatial multi-parameter cellular and sub-cellular imaging data for a tumor of the individual and analyze the patient spatial multi-parameter cellular and sub-cellular imaging data using the joint prognostic model to determine a predicted cancer recurrence risk for the individual. The joint prognostic model has been previously developed and trained by receiving spatial multi-parameter cellular and sub-cellular imaging data for a plurality of cancer patients, spatially dissecting the spatial multi-parameter cellular and sub-cellular imaging data into a plurality of intra-tumor spatial domains, generating a base feature set for each of the intra-tumor spatial domains, for each of the intra-tumor spatial domains, selecting a subset of features from the base feature set for the intra-tumor spatial domain, for each of the intra-tumor spatial domains, developing and training a spatial domain specific multivariate prognostic model for predicting cancer recurrence risk using the subset of features of the intra-tumor spatial domain, and combining the spatial domain specific multivariate prognostic model of each of the intra-tumor spatial domains into the joint prognostic model for predicting cancer recurrence risk.

In still another embodiment, an apparatus for predicting cancer recurrence risk for an individual is provided that includes a computer system comprising a processing apparatus implementing a prognostic model for predicting cancer recurrence risk. The processing apparatus is structured and configured to receive patient spatial multi-parameter cellular and sub-cellular imaging data for a tumor of the individual, and analyze the patient spatial multi-parameter cellular and sub-cellular imaging data using the joint prognostic model to determine a predicted cancer recurrence risk for the individual, wherein the joint prognostic model is based on spatial correlation statistics among a plurality of features derived for a plurality of intra-tumor spatial domains from spatial multi-parameter cellular and sub-cellular imaging data obtained from a plurality of cancer patients.

In yet another embodiment, a method of predicting cancer recurrence risk for an individual is provided that includes receiving patient spatial multi-parameter cellular and sub-cellular imaging data for a tumor of the individual, and analyzing the patient spatial multi-parameter cellular and sub-cellular imaging data using a prognostic model for predicting cancer recurrence risk to determine a predicted cancer recurrence risk for the individual, wherein the joint prognostic model is based on spatial correlation statistics among features derived for a plurality of intra-tumor spatial domains from spatial multi-parameter cellular and sub-cellular imaging data obtained from a plurality of cancer patients.

BRIEF DESCRIPTION OF THE DRAWINGS

FIGS. 8A1 through 8C2 are a schematic representation of the base feature set generated according to an exemplary embodiment of the disclosed concept;

DETAILED DESCRIPTION OF THE INVENTION

Figure 1:
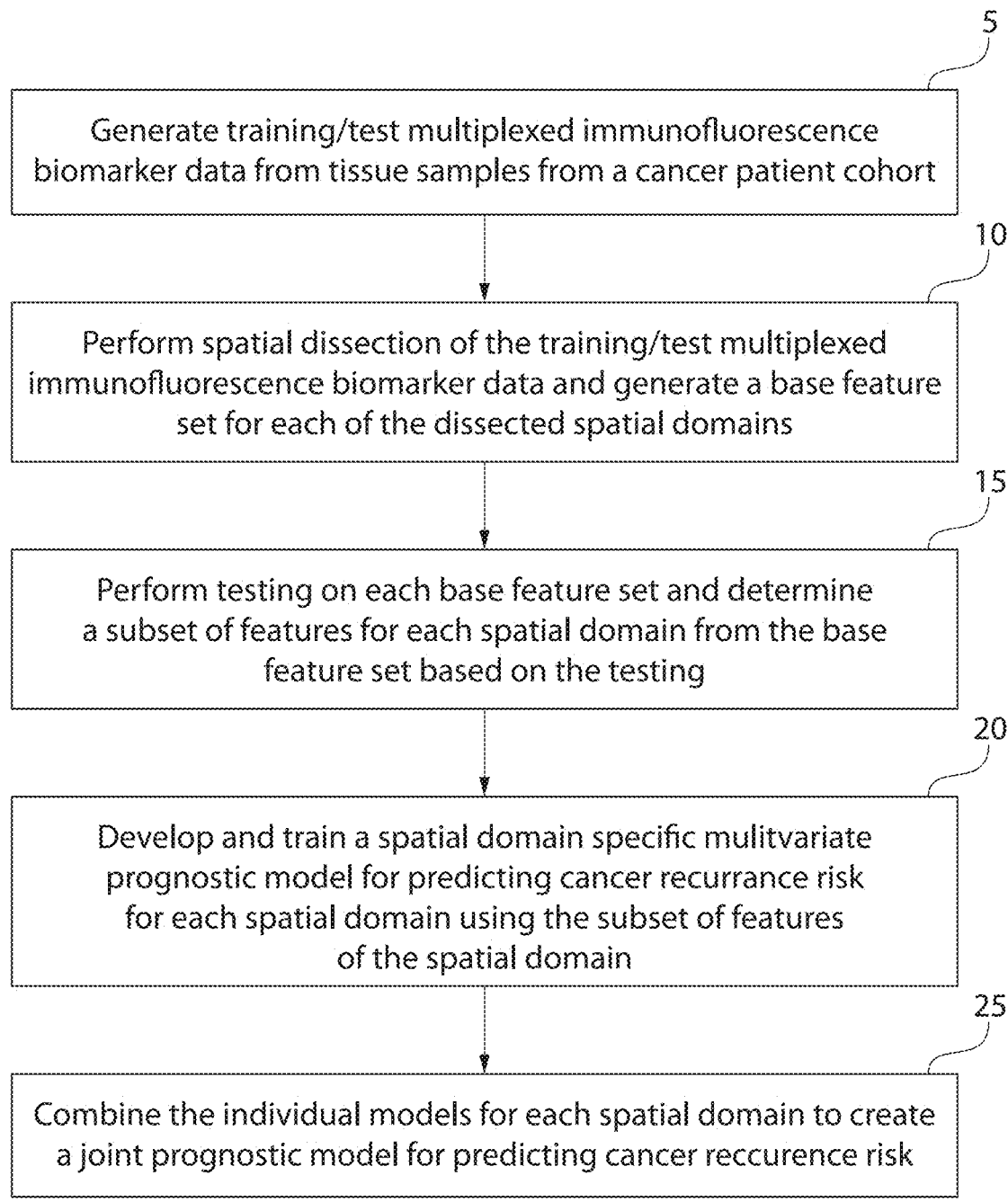
FIG. 1 is a flowchart of a method of developing and training a spatial domain specific multivariate prognostic model for predicting cancer reoccurrence risk according to an exemplary embodiment of the disclosed concept.

As used herein, the singular form of "a", "an", and "the" include plural references unless the context clearly dictates otherwise.

As used herein, the term "number" shall mean one or an integer greater than one (i.e., a plurality).

As used herein, the terms "component" and "system" are intended to refer to a computer related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers. While certain ways of displaying information to users are shown and described with respect to certain figures or graphs as screenshots, those skilled in the relevant art will recognize that various other alternatives can be employed.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The disclosed concept will now be described, for purposes of explanation, in connection with numerous specific details in order to provide a thorough understanding of the subject innovation. It will be evident, however, that the disclosed concept can be practiced without these specific details without departing from the spirit and scope of the disclosed concept.

As described in greater detail herein, the disclosed concept provides, in various embodiments, a novel system and method for predicting the recurrence risk for cancer patients from spatial multi-parameter cellular and sub-cellular imaging data obtained from primary tumors spatial correlation statistics obtained therefrom by identifying emergent spatial domain networks associated with recurrence. In the exemplary embodiment, the disclosed concept is described herein in connection with predicting the recurrence risk for cancer patients from primary tumors with multiplexed immunofluorescence (IF) biomarkers and their spatial correlation statistics, and thus that exemplary embodiment employs multiplexed immunofluorescence biomarker data. It will be understood, however, that the disclosed concept works on any spatial multi-parameter cellular and sub-cellular imaging data, which include, without limitation, the following image modalities: transmitted light, combination of H&E and IHC (1 to multiple biomarkers); fluorescence; immunofluorescence (included but not limited to antibodies, nanobodies); live cell biomarkers multiplexing, hyperplexing; mass spectrometry (including but not limited to CyTOF); spatial transcriptomics (included but not limited to FISH); and electron microscopy.

In particular, in connection with the exemplary embodiment, a deeper understanding of the TME may arise from imaging methods capable of labeling >7 cellular and tissue components in the same sample (hyperplexed (HxIF) fluorescence and other imaging modalities). To fully extract the intrinsic information within each primary tumor, the disclosed concept employs a spatial analytics (SpAn) computational and systems pathology platform applicable to all solid tumors to analyze the spatial relationships throughout TME signaling networks. As described in greater detail herein, the SpAn platform of the disclosed concept constructs a computationally unbiased and clinical outcome-guided statistical model enriched for a subset of TME signaling networks that are naturally selected as dependencies of the corresponding malignant phenotype.

More specifically, according to an aspect of the disclosed concept described in greater detail herein, a spatial domain specific multivariate prognostic model for predicting cancer recurrence risk is developed and trained using multiplexed immunofluorescence biomarker data (e.g., HxIF data) obtained from a large number of cancer patient tissue samples. Thereafter, the trained spatial domain specific multivariate prognostic model may be used to predict risk of cancer recurrence based on multiplexed immunofluorescence biomarker data obtained from tissue sample(s) of an individual patient. In one non-limiting exemplary embodiment described herein, the disclosed concept is able to predict 5-year risk of CRC recurrence in patients with resected primary tumor that also enables inference of recurrence-specific network biology.

FIG. 1 is a flowchart of a method of developing and training a spatial domain specific multivariate prognostic model for predicting cancer reoccurrence risk according to an exemplary embodiment of the disclosed concept. Referring to FIG. 1, the method begins at step 5, wherein multiplexed immunofluorescence biomarker data (i.e., training/test data) is generated from tissue samples from a cancer patient cohort. More specifically, in the exemplary embodiment, a plurality of HxIF image stacks are generated from formalin-fixed paraffin-embedded (FFPE) tissue microarrays (TMAs) from resected tissue samples obtained from the cancer patient cohort. As will be appreciated, generation of the HxIF image stacks involves, for each stack, the generation of a plurality of high resolution multiplexed images from each tissue section using a multiplexed (specifically hyperplexed in this embodiment) imaging process that includes repeated labeling of each tissue section with a number of fluorescent tags to image a plurality of biomarkers.

In the non-limiting exemplary embodiment, the training/test multiplexed immunofluorescence biomarker data acquired in step 5 of FIG. 1 may be generated using the GE Healthcare Cell DIVE™ (previously named MultiOmyx) HxIF imaging and image processing workflow instrument. The Cell DIVE™ system can perform hyperplexed imaging of greater than 50 biomarkers via sequentially multiplexed imaging of 2 to 3 biomarkers plus DAPI (4',6-diamidino-2-phenylindole) nuclear counterstain through iterative cycles of label-image-dye-inactivation. Extensive validation of this approach has demonstrated that a majority of epitopes tested are extremely robust to the dye inactivation process. It has been found that the biological integrity of the samples is preserved for at least 50 iterative cycles.

In one particular non-limiting exemplary embodiment of the disclosed concept described herein for illustrative purposes, 55 particular biomarkers are used to generate the training/test multiplexed immunofluorescence biomarker data in step 5. It will be appreciated, however, that this is meant for illustrative purposes only and that more or less and/or different biomarkers may also be used within the scope of the disclosed concept. The particular biomarkers of this exemplary illustrative implementation are shown in Table 1 below, and include markers for epithelial, immune and stromal cell lineage, subcellular compartments, oncogenes, tumor suppressors, and posttranslational protein modifications indicative of cellular activation states.

TABLE 1

| | |
|---|---|
| p4EBP1 | Eukaryotic initiation factor 4E binding protein one: inhibits mRNA translation initiation/phosphorylation relieves inhibition of mRNA translation initiation. |
| AKT | Signal transduction: cell survival/anabolic metabolism |
| Albumin | Extracellular transport: binds drugs and small metabolites |
| ALDH1 | Cytosolic aldehyde dehydrogenase/retinoic acid metabolism/alcohol Metabolism |
| BetaActin | Microfilament protein: structure and motility |
| BetaCatenin | Adherens junctions/Wnt signaling |
| CA9 | Membrane associated carbonic anhydrase: Hypoxia response/pH modulation |
| CD20 | B-lymphocyte protein of unknown function |
| CD31 | Endothelial cell: cell junctions/immune cell trans endothelial migration |
| CD68 | Tissue macrophage scavenger receptor/endosomal-lysosomal glycoprotein/selectin-dependent migration |
| CD79 | B-lymphocyte antigen receptor complex - mediates antigen dependent B-lymphocyte activation and signal transduction |

TABLE 1-continued

| | |
|---|---|
| CD8a | Antigen recognition/class I MHC binding/T-lymphocyte mediated killing |
| CK1, 5, 6, 8 (pck26) | Pan-cytokeratin: recognizes most basal and luminal epithelial cell subtypes |
| CK19 | Cytokeratin 19: unpaired with basic cytokeratin Useful for identification of epithelium and epithelial malignancies including adenocarcinomas of colon, stomach, pancreas, biliary tract, liver, breast, and thyroid carcinoma of the papillary type |
| Claudin1 | Epithelial and endothelial tight junction protein/epithelial barrier function/homo and heteropolymers and zona occludins protein binding. Neu- trophil expression in CRC. Colocalizes with neutrophil specific elastase |
| Cleaved Caspase 3 | Cysteine peptidase - active form: activation of apoptosis/possible role in lipid metabolism through activation of SREBP |
| E-cadherin | Epithelial specific homotypic adherens junctions/Wnt signaling/epithelial-mesenchymal transition/calcium dependent cell- cell adhesion/E7 integrin ligand |
| EGFR | Epidermal growth factor receptor: receptor tyrosine kinase/binds epithelial growth factor/homo or heterodimerization/activates signal transduction |
| EPCAM | Epithelial cell adhesion molecule: homotypic calcium independent cell adhesion molecule/cell cycle modulation (myc, cyclin A and E) |
| ERK | Mitogen activated protein kinase 1: central hub of mitogenic-progrowth signaling |
| EZH2 | Polycomb repressor complex two methyltransferase: inactivates gene expression through histone acetylation on H3K9 and H3K27 |
| Fibronectin | Secreted cell adhesion protein involved in basement membrane function |
| FOXO1 | Forkhead Box-O1: transcription factor involved in regulating intermediary metabolic enzymes and cell survival |
| FOXO3a | Forkhead Box-O3a: transcription factor involved in regulating intermediary metabolic enzymes and cell survival |
| GLUT1 | Facilitated glucose/aldose uptake: upregulated in cancer cells/aerobic glycolysis/Warburg effect |
| Indian Hedge Hog | Hedgehog/patched/smoothened signaling: involved in regulating bone metabolism (ossification). |
| Lamin A/C | Nuclear lamin protein: involved in organizing nuclear pores and chromatin |
| MLH1 | MutL homolog one: mismatch repair enzyme Used for differential identification of colorectal carcinoma. Deficiency of MLH-1 is associated with the onset of HNPCC |
| Na+/K+-ATPase | Sodium potassium antiporter - ATP dependent: regulates membrane potential polarization/constitutive expression in all known cell types |
| NDRG1 | nMyc Downstream Regulated One: involved in cytoskeletal dynamics/adherens junctions/metabolism/poorly characterized |
| p-p38MAPK | Mitogen-Activated Protein Kinase 14: integrates stress signals from environmental and cytokine stimuli/phosphorylation indicates the kinase is active. |
| p21 | Cyclin dependent kinase inhibitor. |
| pEGFR | Epidermal growth factor receptor: receptor tyrosine kinase/binds epithelial growth factor/homo or heterodimerization/activates signal transduction |
| pERK 1/2 | Mitogen activated protein kinase 1/2: central hub of mitogenic- progrowth signaling/this phosphorylation on the residues targeted here is indicative of kinase activity Reference: |
| pGSK3a | Glycogen synthase kinase alpha: probable component of the destruction com-plex (-catenin degradation)/phosphorylation on the residue targeted here in- activates the kinase though the creation of a pseudosubstrate |
| pGSK3beta | Glycogen synthase kinase beta: known component of the destruction complex (-catenin degradation)/phosphorylation on the residue targeted here inactivates the kinase though the creation of a pseudosubstrate |
| pMAPKAPK2 | Mitogen-Activated Protein Kinase-Activated Protein Kinase 2: p38MAPK substrate motif/active MAPKAPK2 stabilizes TNF and IL6 mRNA/destabilizes HSP27complexes |
| pMET | Met Proto-Oncogene (Hepatocyte Growth Factor Receptor): instigates signaling through prosurvival and EMT signaling pathways/expression is required for gastrulation and deregulated overexpression is common in many cancers/Y1349 phosphorylation serves as a Gab1 binding site (a scaffold for activation of PI3K, PLC, and SHP2) |
| pNDRG1 | nMyc Downstream Regulated One: involved in cytoskeletal dynamics/adherens junctions/metabolism/poorly characterized/phosphorylation of this residue is downstream of mTORC2 |
| pS6 | Ribosomal Protein S6: phosphorylation is associated with mitogens and growth factors and may regulate selective translation of particular classes of mRNAs defined by consensus sequences in untranslated regions. |
| PTEN | Phosphatidylinositol 3,4,5-trisphosphate 3-phosphatase and dual- specificity protein phosphatase PTEN: tumor suppressor/opposes PI3K function by de-phosphorylating the inositol 3'OH group/emerging nuclear functions related to DNA repair and apoptosis |
| S6 | Ribosomal Protein S6: phosphorylation is associated with mitogens and growth factors and may regulate selective translation of particular classes of mRNAs defined by consensus sequences in untranslated regions |
| SMA | Smooth muscle actin alpha: cytoskeletal protein of smooth muscle and vascular pericytes |
| TKLP1 | Transketolase-like protein 1: transfers 2 carbon ketol groups to aldose acceptor molecules (TKTL1) |
| WNT5a | Wnt signaling secreted glycoprotein 5a: signals through canonical and non-canonical Wnt pathways/may affect cell motility and metastasis |

Figure 3:
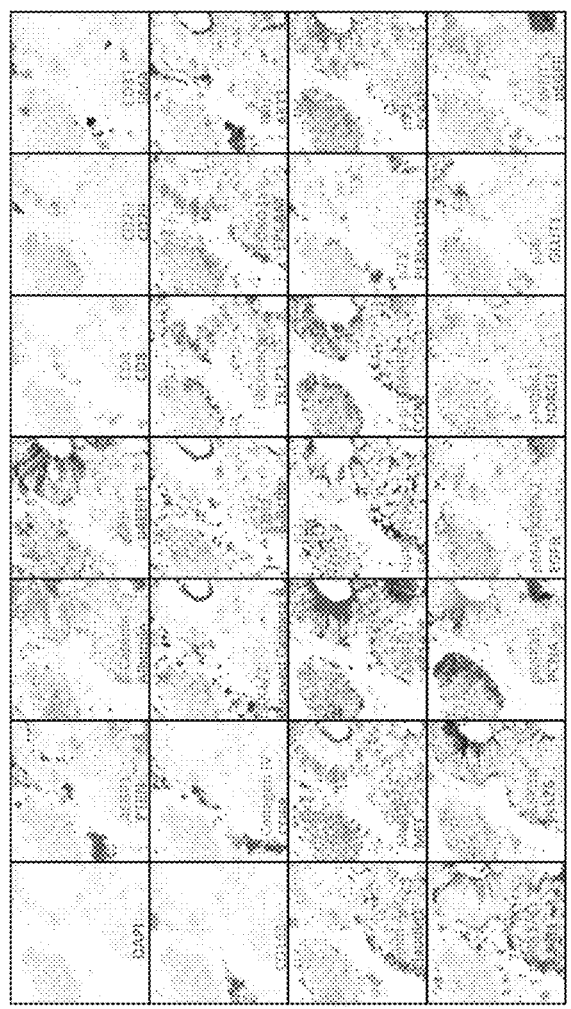
FIG. 3 highlights a sub-region of the patient TMA spot of FIG. 2 enabling optimal visualization of the 55 HxIF biomarker images resulting from the iterative label-image-chemical-inactivation cycles.
Figure 2:
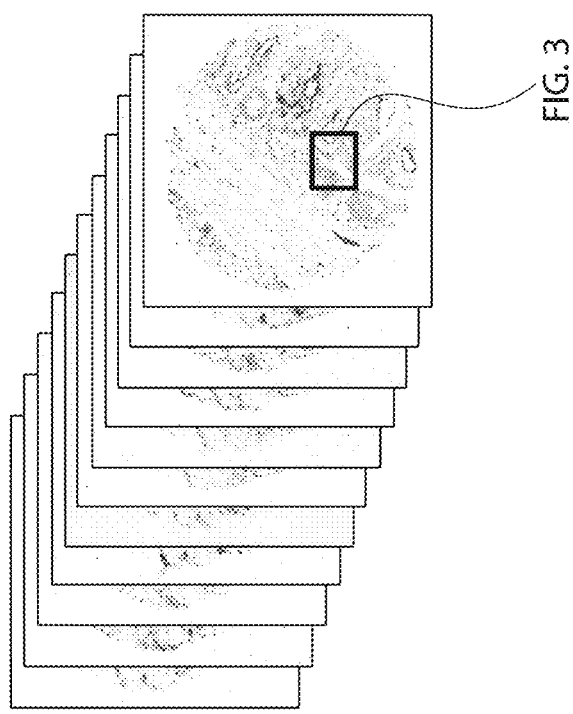
FIG. 2 shows an exemplary HxIF image stack of an exemplary TMA spot from a resected primary tumor of a Stage II CRC patient labelled with the 55 biomarkers plus DAPI of a particular illustrative embodiment of the disclosed concept.

FIG. 2 shows an exemplary HxIF image stack of an exemplary 5 μm thick and 0.6 mm wide TMA spot from a resected primary tumor of a Stage II CRC patient labelled with the 55 biomarkers plus DAPI of this particular illustrative embodiment. FIG. 3 highlights a sub-region of this patient TMA spot enabling optimal visualization of the 55 HxIF biomarker images resulting from the iterative label-image-chemical-inactivation cycles.

In the non-limiting exemplary embodiment, the patient cohort used in step 5 of FIG. 1 was a retrospectively acquired chemo-naïve CRC patient cohort that included patients in Stage I through Stage III of CRC primary tumor growth between the years of 1993 and 2002. The use of a chemo-naïve (no administration of neoadjuvant or adjuvant therapies for the 5+ years of follow-up) CRC patient cohort provides the opportunity to interrogate unperturbed primary tumor biology.

In one particular exemplary embodiment, DAPI based nuclear staining may be used to register and align sequentially labeled and imaged TMA spots prior to downstream image analysis steps. In addition, autofluorescence may be removed from the stained images. In addition, in one particular exemplary embodiment, following single cell segmentation as described herein, several data pre-processing steps may be conducted. These included cell filtering, spot exclusion, log 2 transformation and slide to slide normalization. In this embodiment, cells are included for downstream analysis if their size was greater than 10 pixels at 20× magnification. The hyperplexing process can result in the tissue being damaged, folded or lost. Image registration issues can also result in poor-quality cell data. Therefore, a tissue quality index based on the correlation of that image with DAPI may be calculated for each cell for each round.

Only those cells whose quality index is equal to or greater than 0.9 (meaning that at least 90% of the cells overlapped with DAPI) may then be included. All the slides for all the biomarkers may also be adjusted to a common exposure time per channel. The data may then log 2 transformed. A median normalization that equalizes the medians of all the slides may be performed to remove slide to slide non-biological variability.

Referring again to FIG. 1, following the generation of the training multiplexed immunofluorescence biomarker data at step 5, the method proceeds to step 10. At step 10, spatial dissection is performed on the training/test multiplexed immunofluorescence biomarker data to divide the training/test multiplexed immunofluorescence biomarker data (each image in each stack) into a plurality of intra-tumor spatial domains as described below (e.g., epithelial, stromal and epithelial-stromal). Then, a base feature set (of spatial domain based features) is generated from the dissected multiplexed immunofluorescence biomarker data as described in detail below for each intra-tumor spatial domain. In the exemplary embodiment, the base feature set for each intra-tumor spatial domain includes a plurality of intensity-based feature, such as, without limitation, intensity expression values for specific biomarkers, and/or correlation values for each pair of the biomarkers. The base feature set for each intra-tumor spatial domain may also include other spatial heterogeneity measures such as, without limitation, other spatial analytics ranging from simple to sophisticated spatial heterogeneity metrics and incorporating a combination of protein and nuclei acid biomarkers.

In particular, in the exemplary embodiment, the base feature set for each spatial domain is generated by first performing a virtual three-level spatial-dissection (cell segmentation) of the tumor microenvironment represented by the training multiplexed immunofluorescence biomarker data. This is done by first explicitly segmenting the TMA (each image in each stack) into epithelial and stromal regions, differentiated by epithelial E-cadherin staining. The cells in the epithelial region are identified using E-cadherin cell-cell adhesion labeling and pan-cytokeratin, with individual epithelial cells segmented using a Na+K+ATPase cell membrane marker, ribosomal protein S6 cytoplasmic marker, and DAPI-based nuclear staining. Protein expression level and standard deviation were subsequently quantified in each cell.

Figure 6:
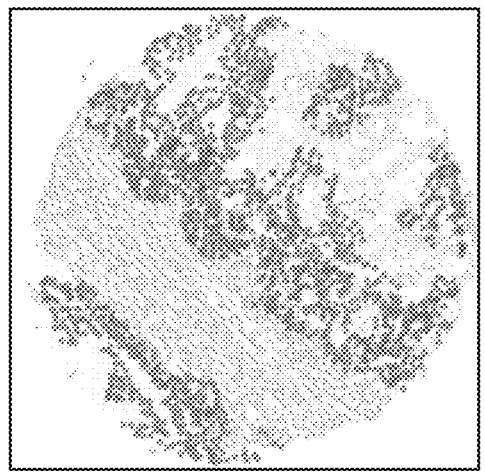
FIG. 6 shows the epithelial-stromal spatial domain of the exemplary TMA spot in FIG. 2.
Figure 5:
FIG. 5 shows the stromal spatial domain of the exemplary TMA spot in FIG. 2.
Figure 4:
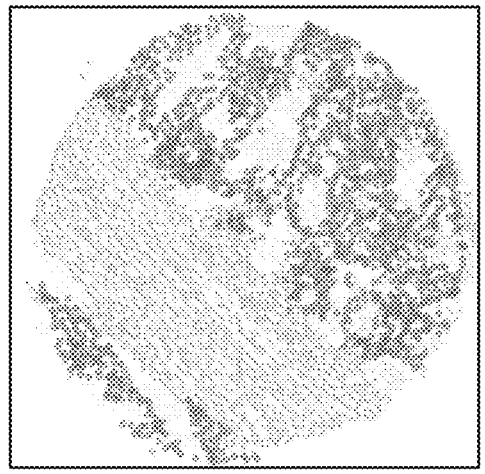
FIG. 4 shows the epithelial spatial domain of the exemplary TMA spot in FIG. 2.
Figure 7:
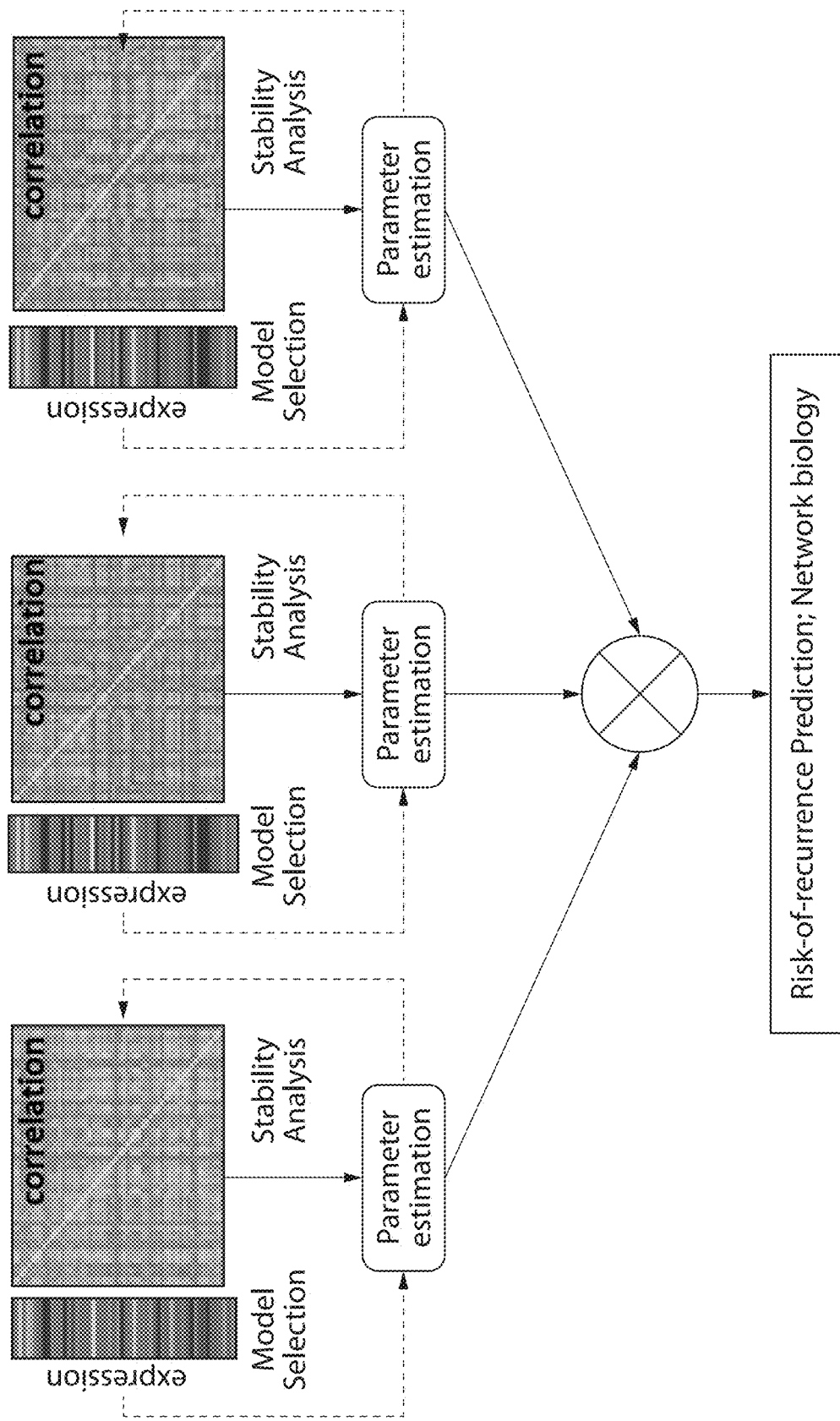
FIG. 7 is a schematic representation of the spatial model of an exemplary embodiment of the disclosed concept.

The resulting epithelial spatial domain of the exemplary TMA in FIG. 2 is shown in FIG. 4. The remaining cells are assigned to the stromal domain and are shown in FIG. 5. These stromal cells have diverse morphologies. Based on the epithelial and stromal domains, the method of the disclosed concept also identifies a third spatial domain, the epithelial-stromal domain, shown in FIG. 6, to explicitly capture a 100 μm boundary wherein the stroma and malignant epithelial cells interact in close proximity. Together, these three intra-tumor spatial domains comprise the virtual three-level spatial dissection of the tumor microenvironment that forms the basis for the spatial model of the disclosed concept shown schematically in overview in FIG. 7 and described in detail herein.

Next, utilizing expression of the 55 hyperplexed biomarkers, the base feature set for each spatial domain is generated by first computing the corresponding 55 mean intensities and 1485 Kendall rank-correlations as features characterizing each of the three spatial domains as shown schematically in FIGS. 8A1 through 8C2. The mean intensity captures the average domain-specific expression profile of each biomarker, while the Kendall rank-correlations measure strength of association between any two biomarkers without presuming linearity. Importantly, computation of domain-specific rank-correlations as explicit features in the disclosed concept is used in place of the more typical approach of implicitly incorporating correlations as interactions between covariates (average biomarker expressions) within the prediction model. These explicit features not only detect the association between two biomarkers presumably mediated by intracellular and intercellular networks all within the same spatial domain, but also by mediators (e.g., exosomes) derived from another spatial domain.

In one particular exemplary embodiment, for each of the epithelial, stromal and epithelial-stromal spatial domains, the disclosed concept uses M=1540 domain-specific biomarker feature vector f as input. This input feature vector is comprised of: (1) the mean intensity value of 55 biomarkers averaged across all cells within the spatial domain, and (2) 1485 (=55*54/2) Kendall rank-correlations between all 55 biomarker pairs within the spatial domain. Kendall rank-correlation was chosen as the correlation metric because it is a non-parametric measure of association between two biomarkers. Moreover, its use of concordant and discordant pairs of rank-ordered biomarker expression for computing correlation coefficients allows it to robustly capture biomarker associations in presence of measurement noise and small sample size. Rank-correlation for each pair of biomarkers is computed for each spatial-domain from all cells across the spatial-domain expressing the biomarkers. This approach is distinctly different from prediction models that typically consider correlations via interactions, implicit within the models, between mean biomarker intensity expressions—with the biomarker expressions being the only covariates of the model. It is emphasized that the disclosed concept does not compute correlations through mean intensity biomarker expression across the spatial-domain, but instead uses biomarker expressions across individual cells of the spatial domain to explicitly compute domain-specific rank-correlation values between every pair of biomarkers to form the base correlation feature set of the disclosed concept.

In addition, before computing these two sets of features, the analysis workflow of the exemplary embodiment includes an initial intensity threshold step to ensure feature robustness. Specifically, the disclosed concept computes intensity-based distribution of cell-level biomarker expression separately for every biomarker across each patient TMA spot. Only intensities above the 85th percentile on this distribution are considered as biomarker expression and included in the computing of the intensity features. This focus on the right-tail of the intensity distribution is deliberately conservative, and although it might potentially exclude low-intensity biomarker expression, it minimizes inclusion of false-positive expressions into the analysis.

Next, after the base feature set for each spatial domain is generated in step 10, the method proceeds to step 15. At step 15, testing is performed on the base feature set for each spatial domain in order to determine a subset of features (optimal features) for each spatial domain from the base feature set.

Figure 9:
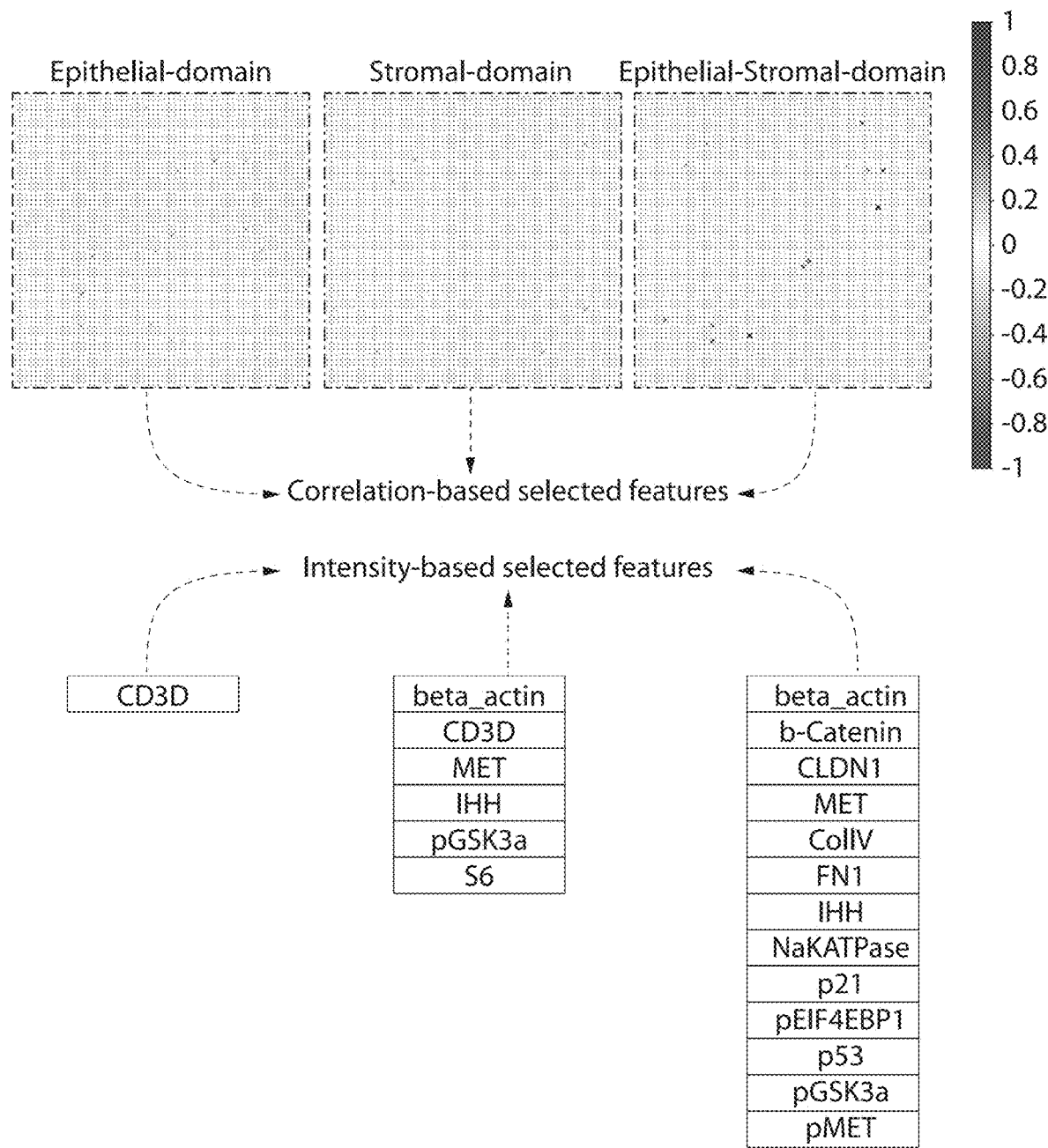
FIG. 9 is a schematic representation, using the representations from FIGS. 8A1 through 8C2, showing how specific optimal spatial domain features are determined from the base feature set via model selection based on an L1-penalized Cox proportional hazard regression method according to an exemplary embodiment of the disclosed concept.
Figure 10A:
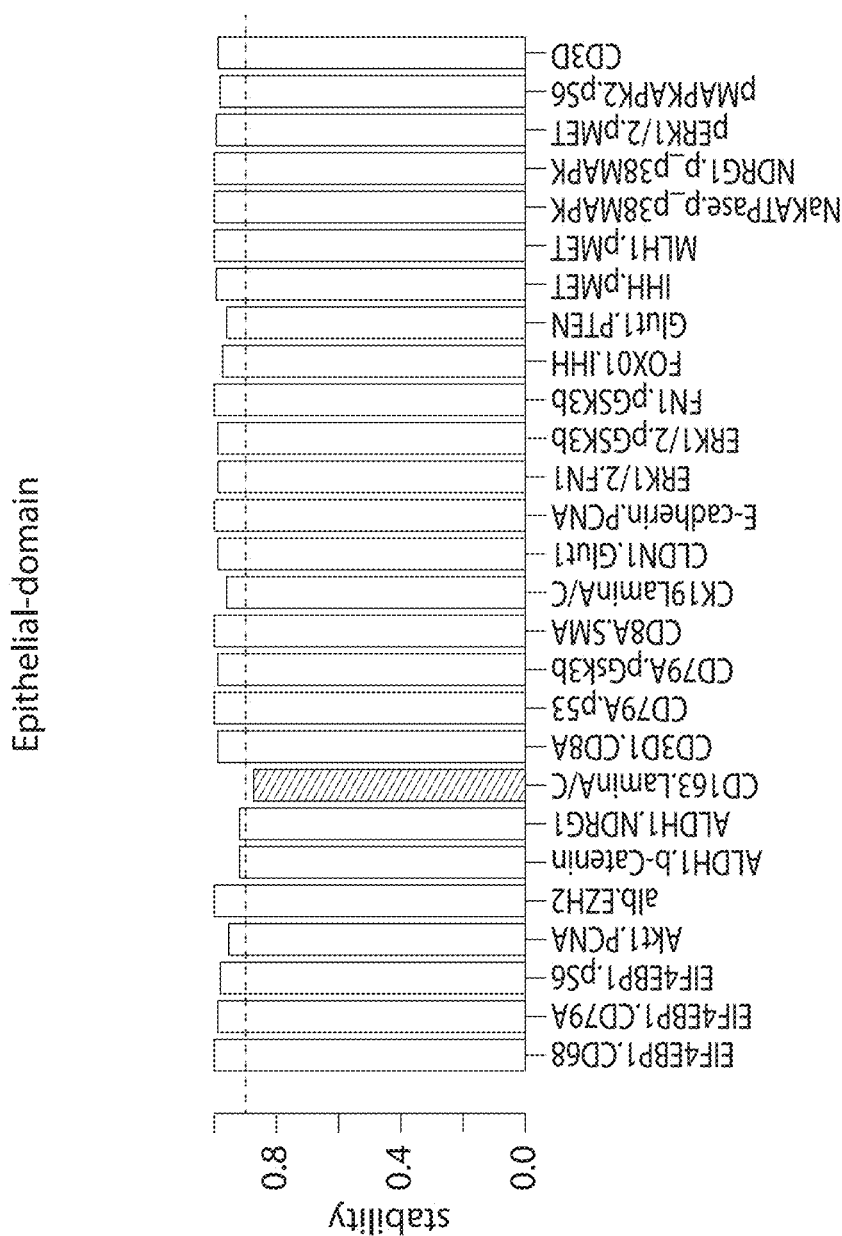
FIGS. 10A, 10B and 10C are a schematic representation showing the final domain-specific features of the optimal subset of features according to an exemplary embodiment of the disclosed concept.
Figure 10B:
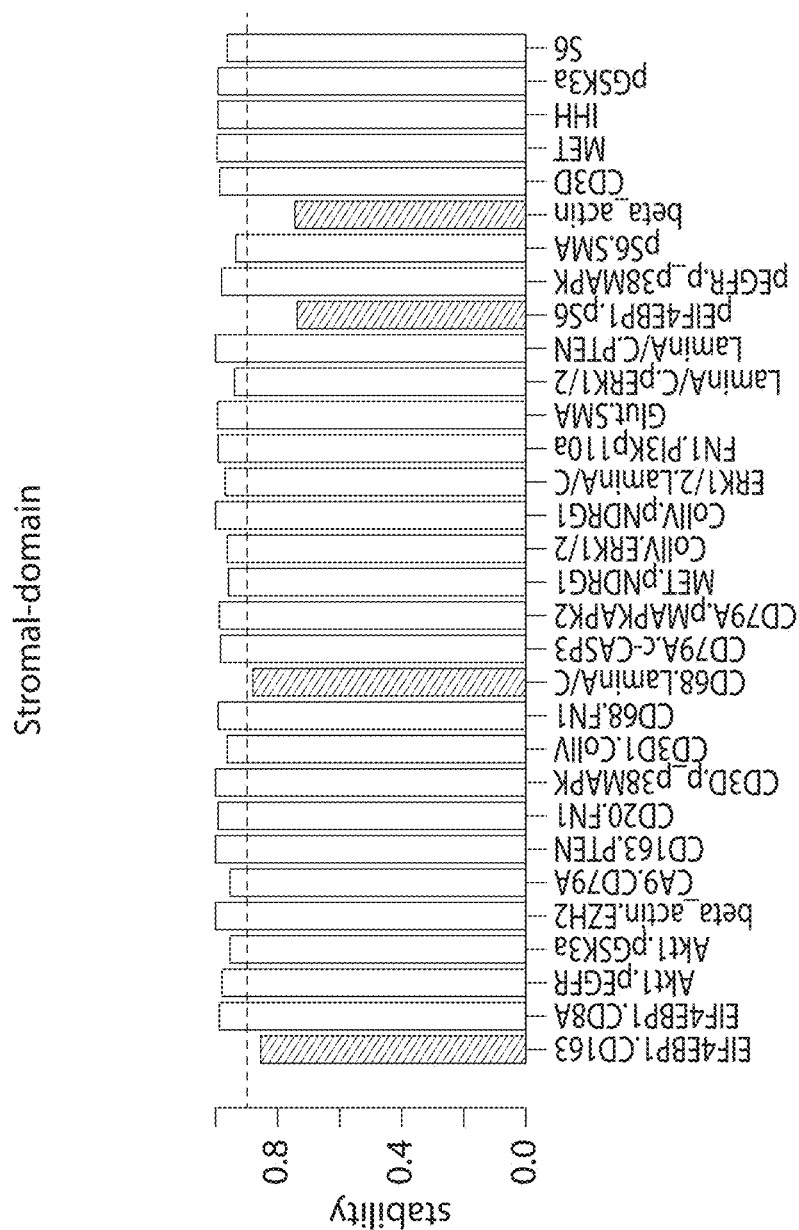
Figure 10C:
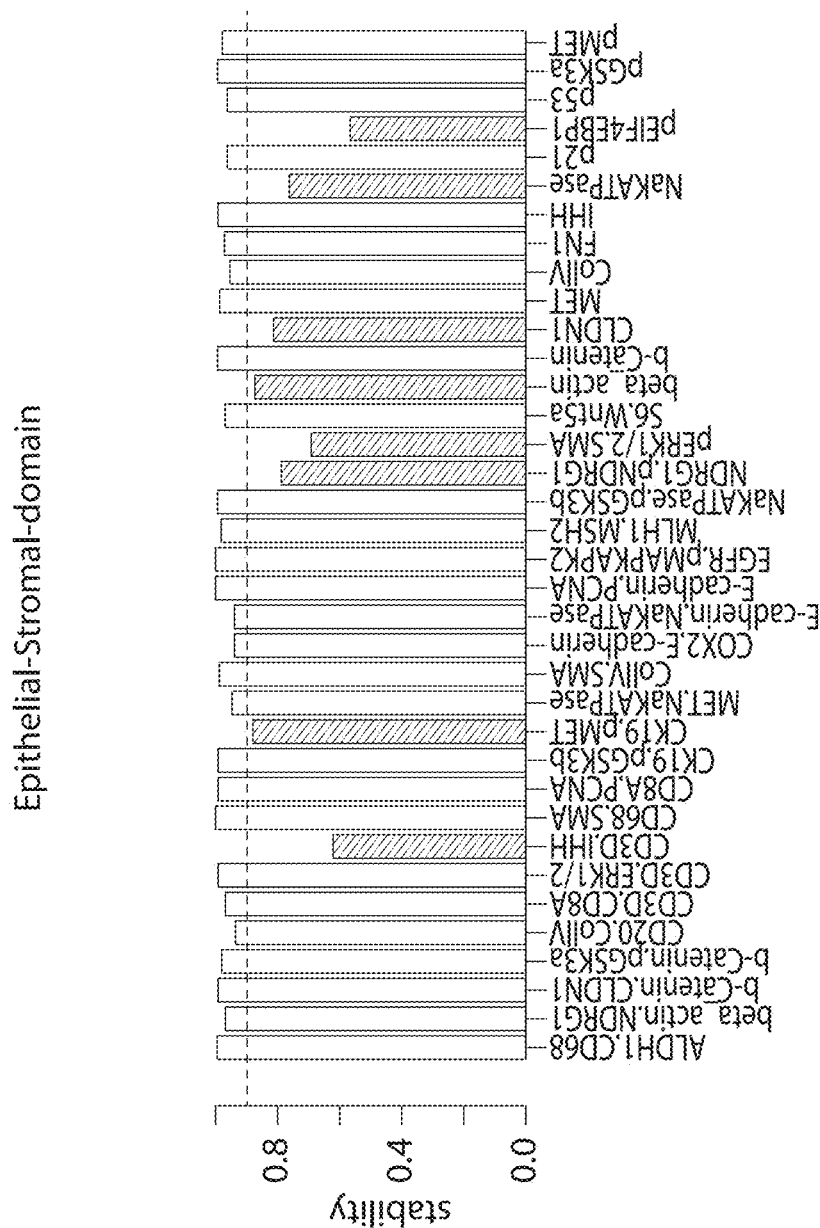

More specifically, in the exemplary embodiment, the disclosed concept uses CRC recurrence-guided learning to determine those specific spatial domain features from the base feature set for each spatial domain that constitute the optimal subset for prognosis via model selection based on an L1-penalized Cox proportional hazard regression method. This process is shown schematically in FIG. 9. A follow-up analysis of the selected features is performed to test the stability of their contribution to recurrence prognosis through testing the stability of the sign of the corresponding coefficients at the 90% threshold. The final domain-specific features of the optimal subset in this exemplary embodiment are shown schematically in FIGS. 10A, 10B and 10C.

Figure 11A:
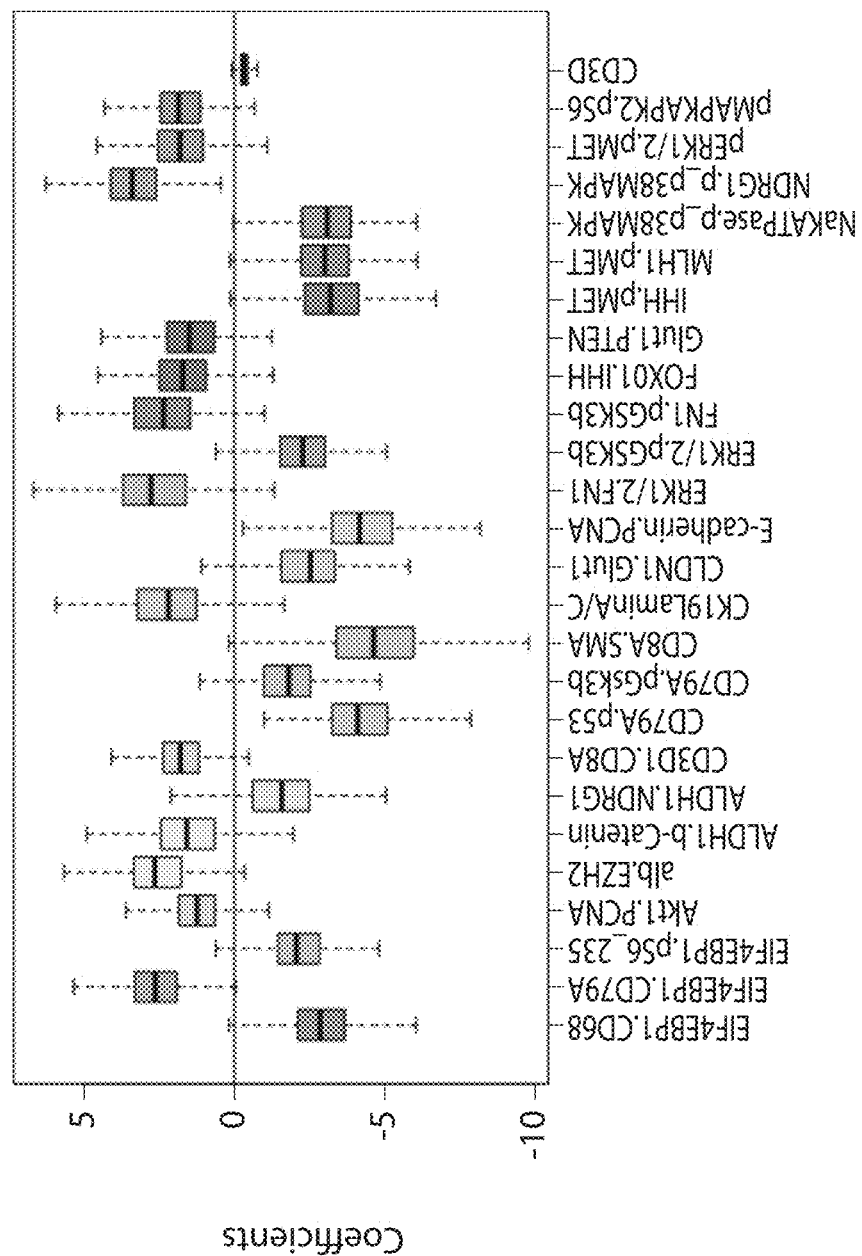
FIGS. 11A, 11B and 11C are a schematic representation showing domain-specific coefficients according to an exemplary embodiment of the disclosed concept.
Figure 11B:
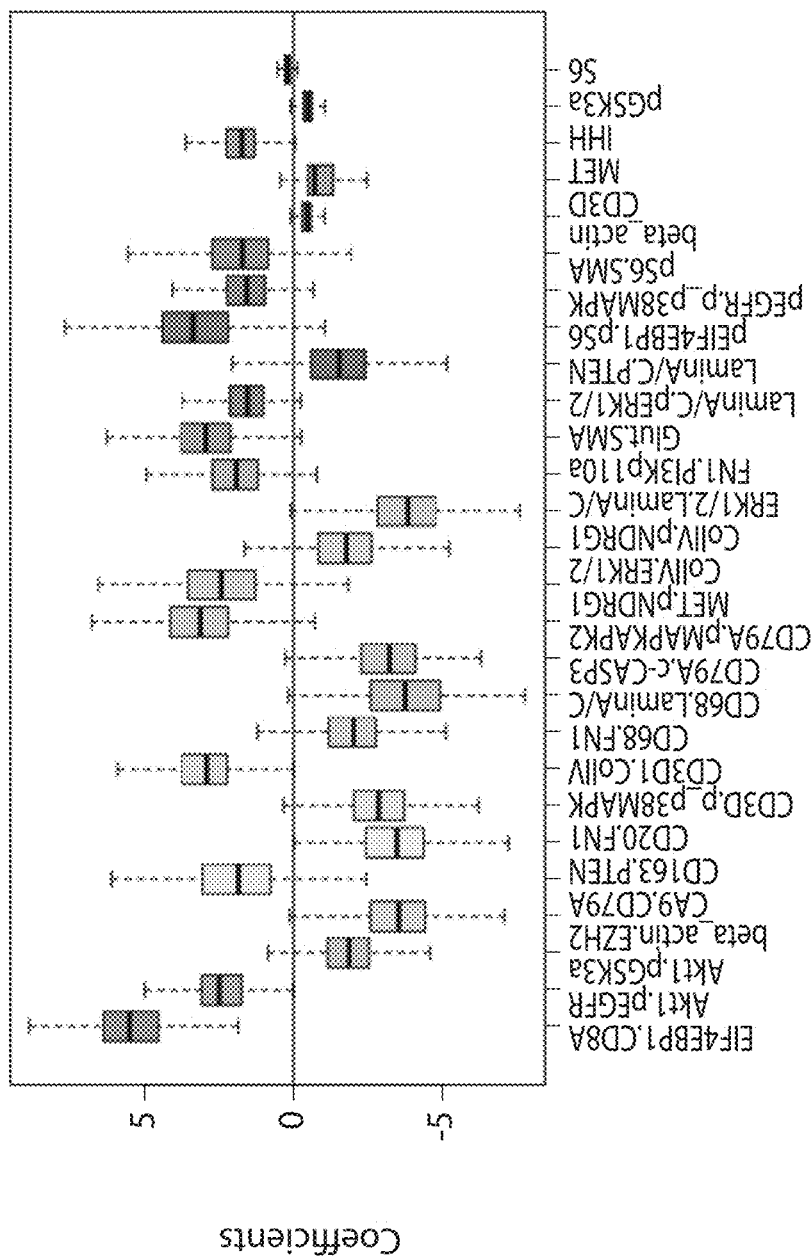
Figure 11C:
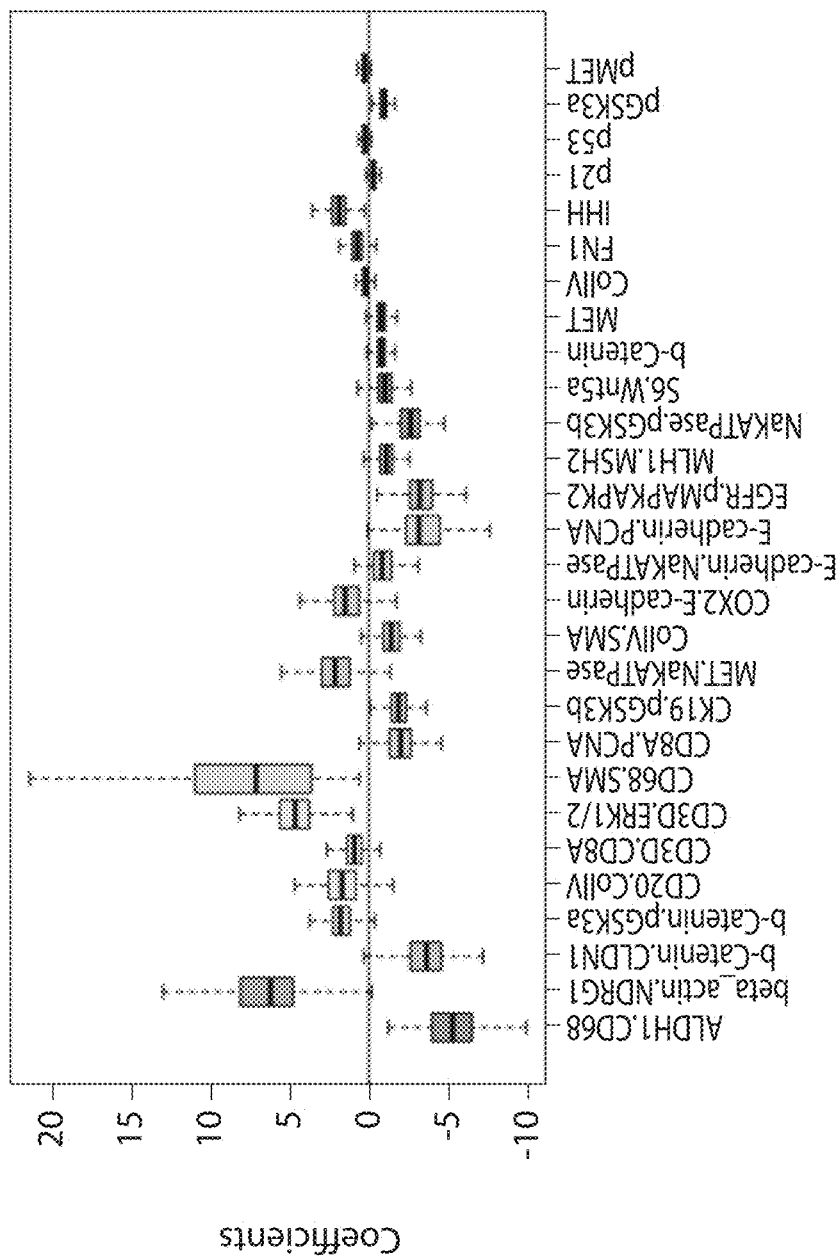

Moreover, the coefficients that control the contribution of the selected features to each of the domain-specific models for assessing recurrence outcome are learned under L1 penalization and their values are, therefore, dependent on all (e.g., 1540) features. To remove this dependence, the disclosed concept relearns each of the three domain-specific model coefficients using L2 penalty in a penalized Cox regression model with only the optimally selected features as input. This L2-regularized learning allows the disclosed concept to estimate optimal contribution of the selected features that are 90% concordant with the recurrence outcome. The resulting domain-specific coefficients of the exemplary embodiment are shown in FIGS. 11A, 11B and 11C.

Next, after the optimal subset of spatial domain features and coefficients for each spatial domain is determined in step 15, the method proceeds to step 20. At step 20, the disclosed concept develops and trains an individual spatial domain specific multivariate prognostic model for predicting cancer recurrence for each spatial domain using the optimal subset of spatial domain features and coefficients of the spatial domain. Then, at step 25, the disclosed concept combines these individual spatial domain specific multivariate prognostic models comprising the optimal domain-specific features weighted by their corresponding coefficients into a single/joint recurrence guided spatial domain prognostic model.

Figure 12:
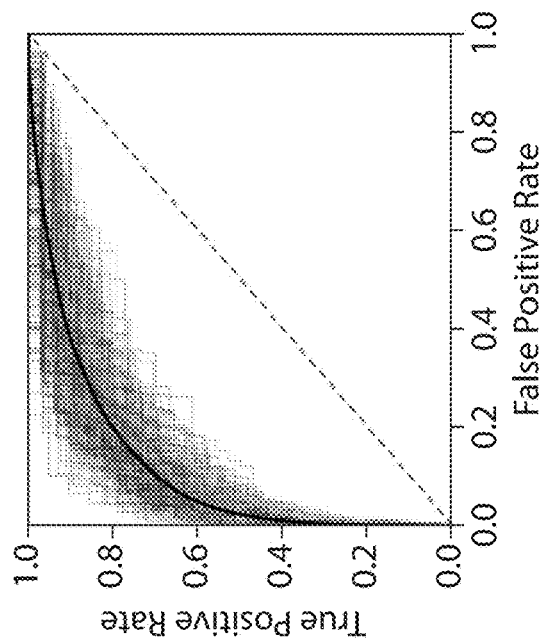
FIG. 12 shows the performance of the spatial domain prognostic model of the disclosed concept according to one particular exemplary embodiment.

The performance of the single/joint model according to one particular exemplary embodiment is shown in FIG. 12. The results were obtained by bootstrapping (sampling with replacement) the patient data set to generate 500 pairs of independent training and testing sets using stratified sampling that ensured the proportion of patients in whom cancer recurred in each of the five years remained the same in each bootstrap. For each bootstrap, the disclosed concept in this embodiment used the training data for learning and the independent testing data to compute the receiver operating characteristic (ROC) curve. These ROC curves are shown in FIG. 12 along with the mean ROC curve. The mean area under the curve (AUC) for bootstrapped ROC curves is 88.5% with a standard error of 0.1%, demonstrating the stable performance of the disclosed concept.

Figure 14:
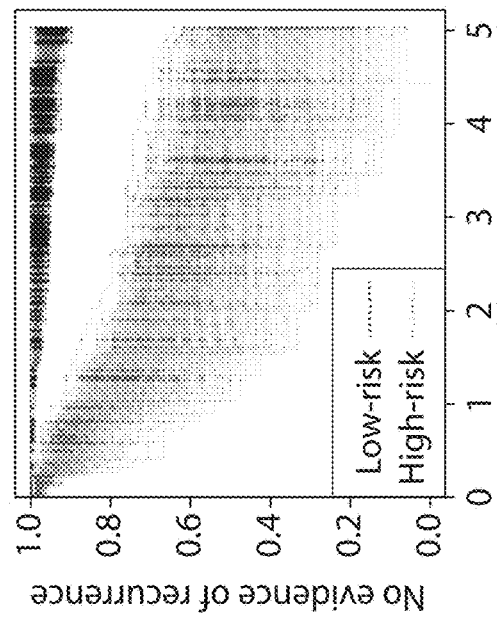
FIG. 14 shows the separation in recurrence-free survival curves of patients identified by the disclosed concept at low- and high-risk of five-year CRC recurrence according to one particular exemplary embodiment.
Figure 13:
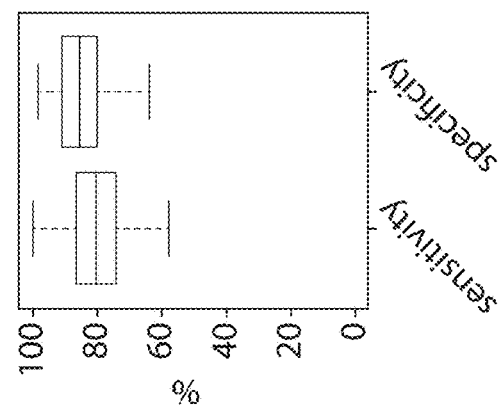
FIG. 13 shows the sensitivity and specificity values for the spatial domain prognostic model of the disclosed concept according to one particular exemplary embodiment.

In one particular embodiment, Youden's index was maximized to identify the clinically relevant operating point on the ROC curves that minimized the overall misdiagnosis rate. FIG. 13 shows the resulting sensitivity and specificity values for all bootstrap runs, with mean values respectively of 80.3% (standard error of 0.4%) and 85.1% (standard error of 0.3%). High specificity limits the disclosed concept from misidentifying no-evidence-of-disease patients as being at high risk of CRC recurrence, while at the same time good sensitivity allows the disclosed concept to not miss high-risk patients. This is emphasized by a high positive likelihood ratio value of 7.2 (standard error of 0.23), which quantifies the large factor by which odds of CRC recurring in a patient go up, when the disclosed concept identifies the patient as at being risk of CRC recurrence. At the same time, a small negative likelihood value of 0.22 (standard error of 0.003) quantifies the decrease in odds of CRC recurrence in a patient when the disclosed concept identifies the patient as being at low-risk. Finally, these results are brought together in FIG. 14, which shows the large separation in recurrence-free survival curves of patients identified by the disclosed concept at low- and high-risk of five-year CRC recurrence.

Furthermore, in one particular, non-limiting exemplary embodiment, in step 15, for each spatial-domain, the disclosed concept implements the Cox proportional hazard model via the partial likelihood function $$L(\beta) = \prod_{k=1}^{K} \frac{e^{(f_{i_k}^T \beta)}}{\sum_{i \in R_k} e^{(f_i^T \beta)}}$$

with the penalty given by $$P_{\lambda,\alpha}(\beta) = \sum_{m=1}^{M} \lambda\left(\alpha|\beta_1| + \frac{1}{2}(1-\alpha)\beta_m^2\right), \text{ and } \alpha = \{0, 1\}.$$

Given feature vector f as input, the partial likelihood $L(\beta)$ quantifies the conditional probability of observing CRC recur in a patient at time $t_k$ (proportional to the numerator $e^{(f_{i_k}^T \beta)}$ of L $(\beta)$), given the risk that a patient will recur from the set $R_k$ of patients at risk at time $t_k$ (proportional to the denominator $$\sum_{i \in R_k} e^{(f_i^T \beta)},$$

over all time $t_k$, k=1, . . . , K,) as quantified by the product over time index k. The partial likelihood is a function of the coefficient vector $\beta$, whose penalized estimate is then used to compute the proportional hazard ratio $HR=e^{(f^T \beta)}$. In this embodiment, the disclosed concept computes this estimate via a two-step process: (1) model selection based on L1-penalized (LASSO) Cox regression where $\alpha$ is set to 1 in penalty $P_{\lambda,\alpha}(\beta)$, followed by (2) L2-regularized $\beta$ estimation, with $\alpha$ set to 0 in the penalty term. As part of model selection, the disclosed concept in this embodiment selects the model that maximally explains the deviance of the null model (model with only intercept and no predictive features) from the biased but perfect model with an exact fit to the recurrence data. Due to the LASSO penalty, the resulting optimal model forces the coefficients of vector $\beta$ that correspond to features that play a minimal role in predicting risk of recurrence to zero. The subset of features with non-zero coefficients defines the selected model. However, to ensure that this subset identifies a stable set of features, the disclosed concept in this embodiment repeats model selection over 500 bootstraps, and includes only those features that were stably concordant at the 90% level with the recurrence outcome. The values of coefficients corresponding to the features stably selected using L1-penalized Cox regression, however, are conditioned on the 1540 input features. As noted elsewhere herein, to remove this dependence, the second step of the disclosed concept in this embodiment described above re-estimates the beta coefficients corresponding to the selected features only, by maximizing the partial likelihood function with L2-regularization as the penalty. The resulting beta-coefficients is passed through a final stability check, where the stability of the coefficient sign in 90% of the 500 bootstrap runs is tested, and only features that pass this threshold are included in the spatial domain model. The disclosed concept in this embodiment performs this process independently for each of the three spatial-domains resulting in domain-specific recurrence-guided features (FIGS. 10A-10C) and their coefficients (FIGS. 11A-11C).

Moreover, in one particular, non-limiting exemplary embodiment, each of the three recurrence-guided domain-specific models defines a hazard risk given by $e^{(f^T epithelial \beta_{epithelial})}$, $e^{(f^T stromal \beta_{stromal})}$ and $e^{(f^T epi-stromal \beta_{epi-stromal})}$ for the epithelial, stromal, and epithelial-stromal domains respectively. The disclosed concept in this embodiment then defines the final overall risk of recurrence model as $$\prod_s \in s^{e^{(f_s^T \beta_s)}},$$

with S={epithelial, stromal, epi-stromal}.

Figure 15A:
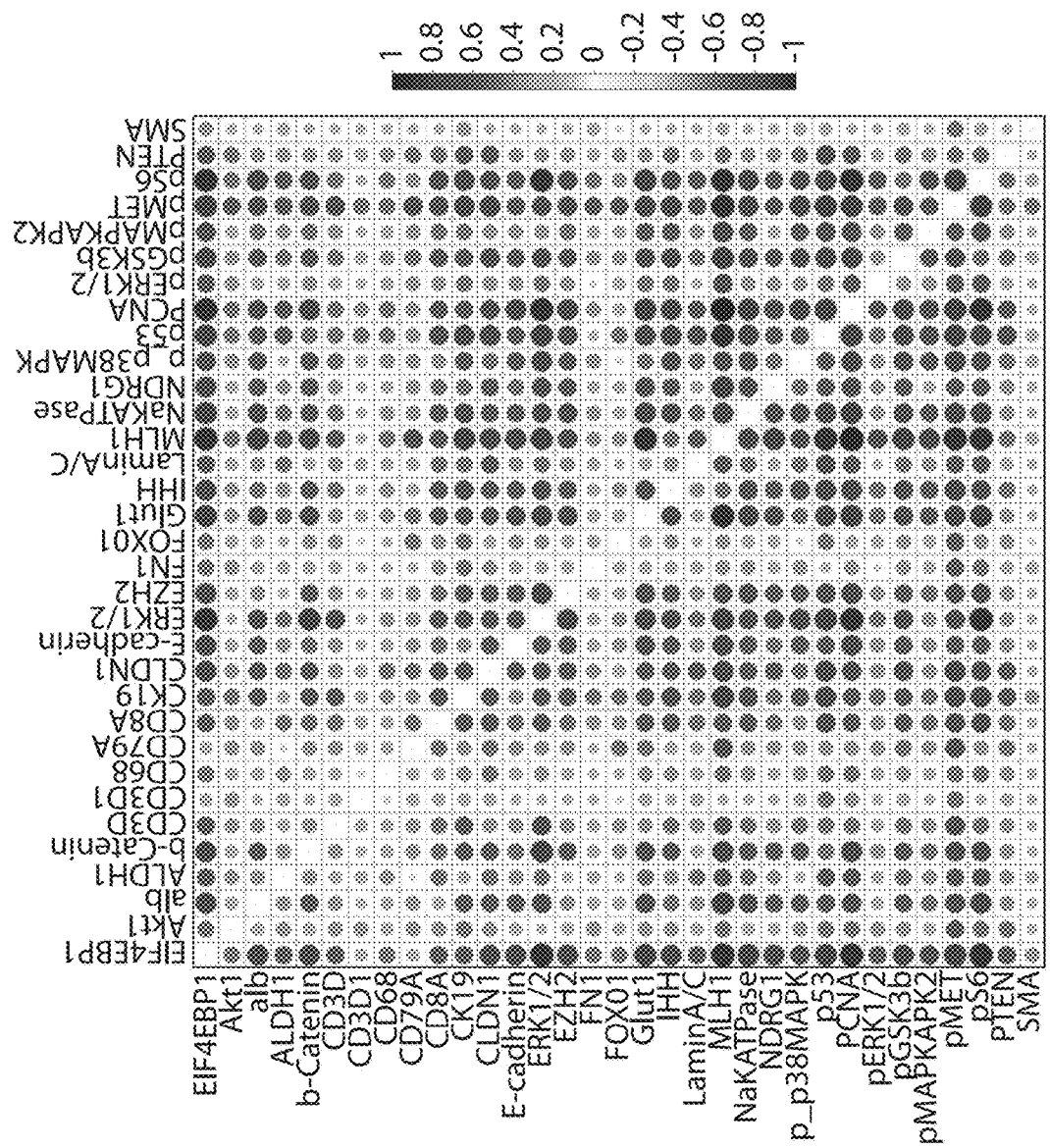
FIGS. 15A-15C show information distance matrices three spatial domains according to one particular exemplary embodiment.
Figure 15B:
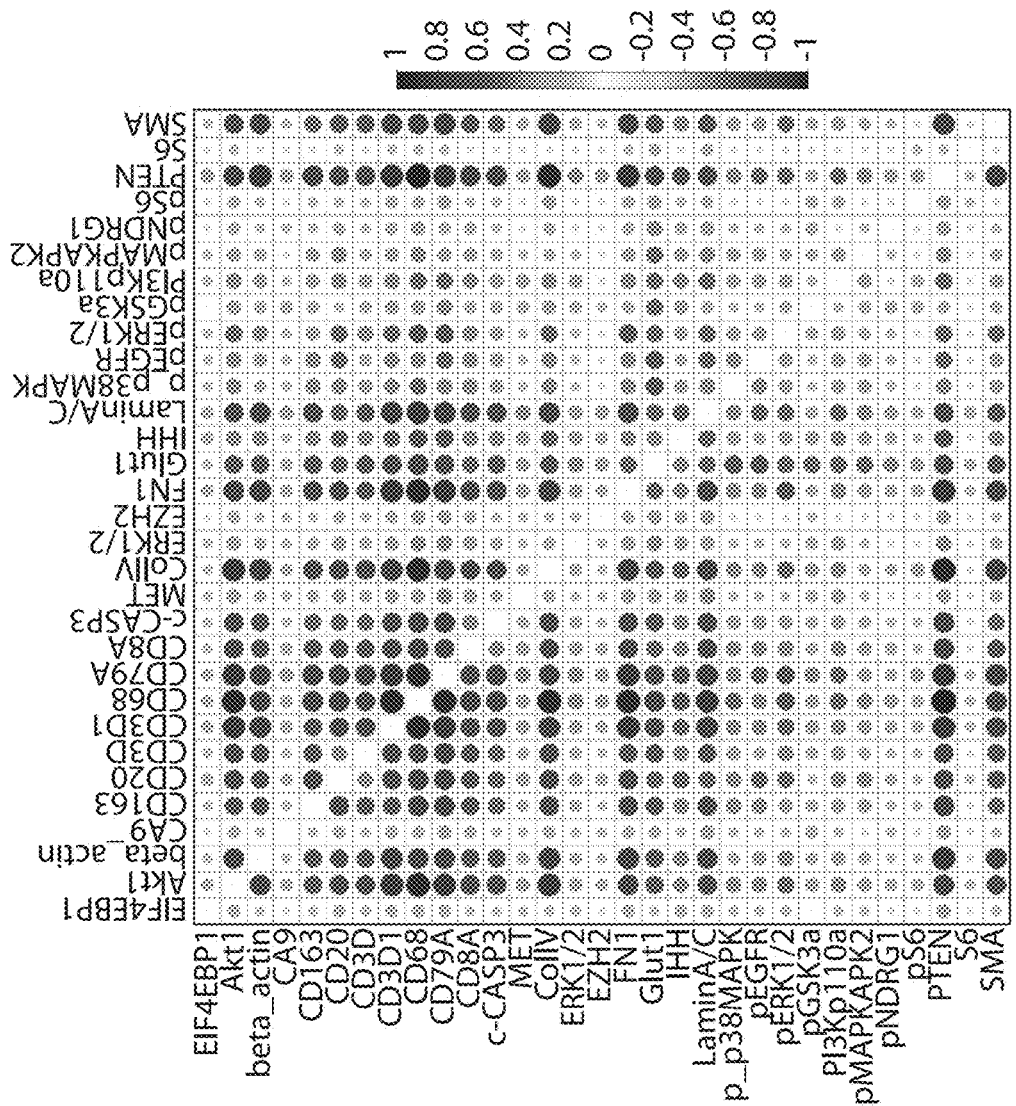
Figure 15C:
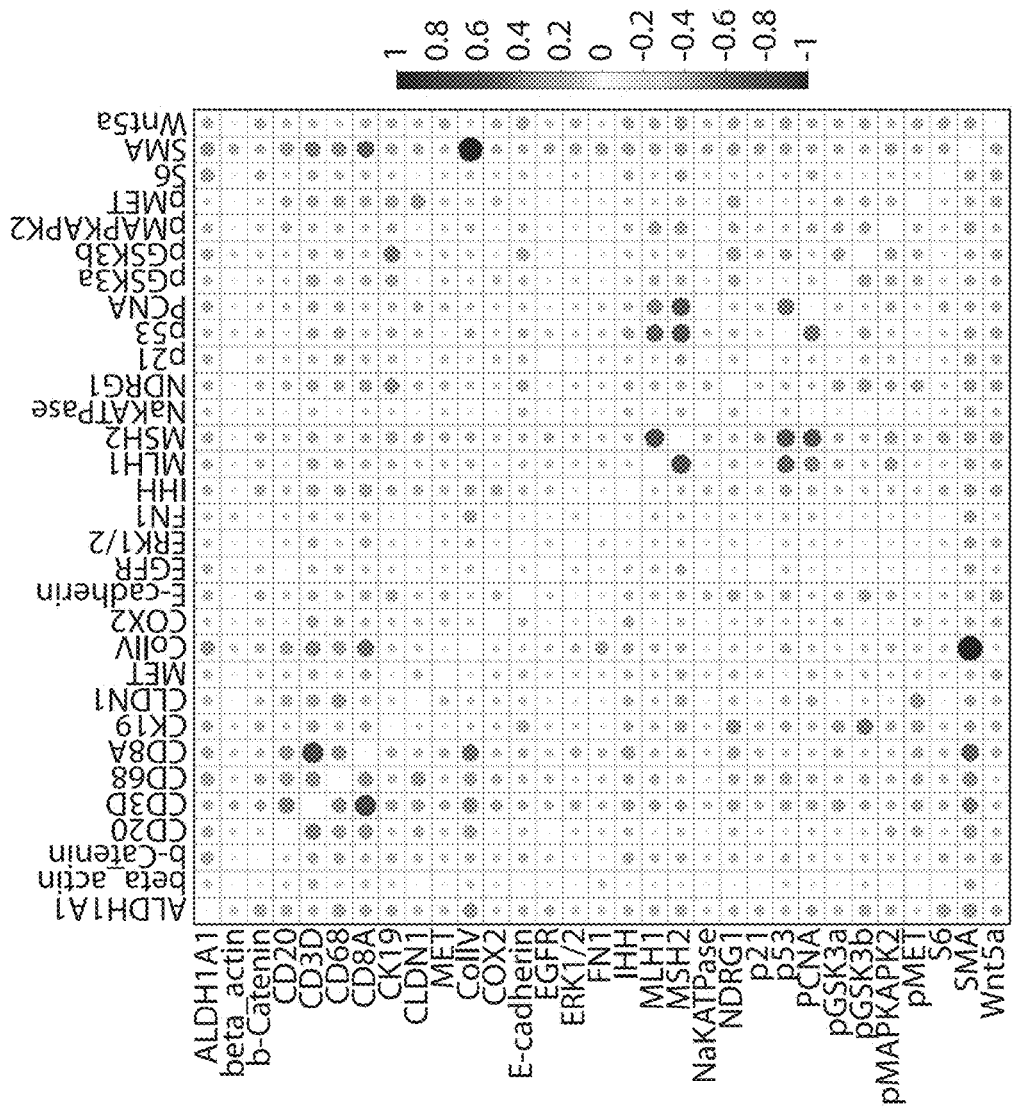
Figure 15F:
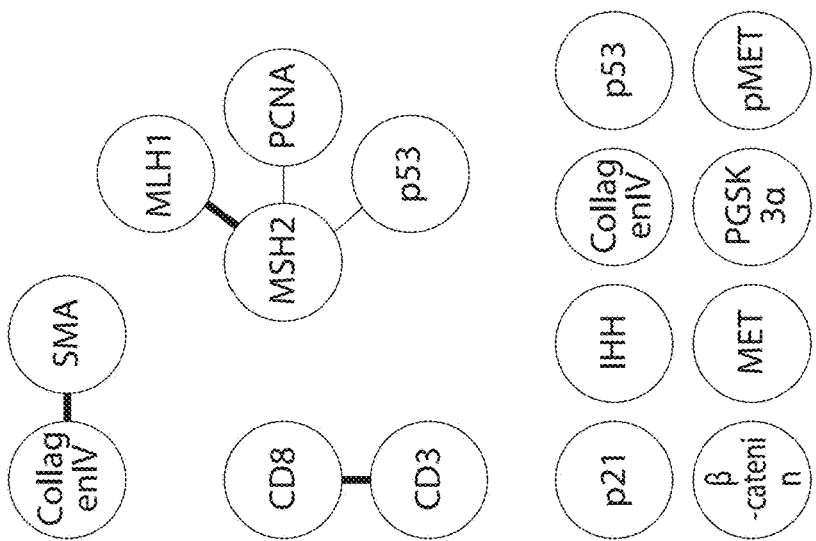
FIGS. 15D-15F show computationally inferred spatial-domain networks according to one particular exemplary embodiment.
Figure 15E:
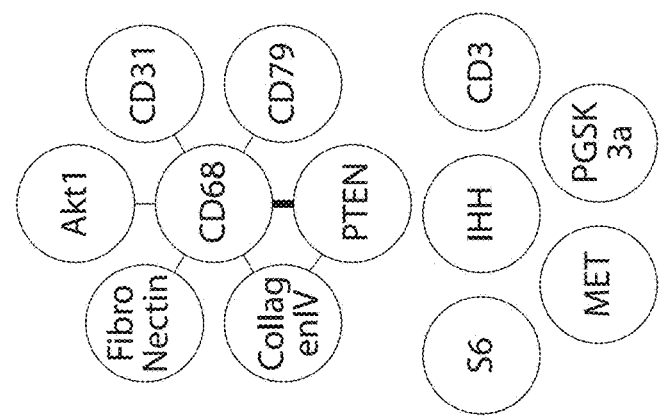
Figure 15D:
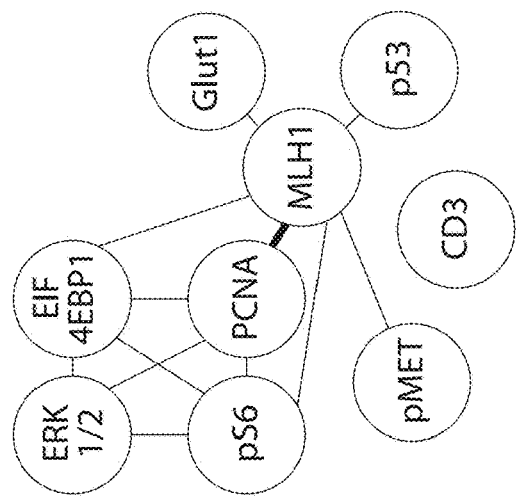

As described herein, for each spatial domain, the selected features identify a set of biomarkers specific to predicting risk of CRC recurrence. The disclosed concept uses them to define a space of biomarkers within which partial correlations between every pair is computed by controlling for confounding effect of biomarkers not defining the pair. The process performed on each patient in one exemplary embodiment is as follows: Let the set of biomarkers identified by the selected features be N (<=55). Using the already computed Kendall rank-correlations between the 55 biomarkers, an N×N correlation matrix C corresponding to the N biomarkers was constructed, with small shrinkage-based modification to guarantee its positive definiteness, and therefore, its invertibility. Next, the N×N precision matrix P is computed by inverting C. The partial correlation between any two biomarkers $bm_i$ and $bm_j$ within the set identified by the selected features, is then computed using $$\rho_{bm_i, bm_j} = \frac{-p_{bm_i, bm_j}}{\sqrt{p_{bm_i, bm_i} \cdot p_{bm_j, bm_j}}},$$

where $p_{bm_i, bm_j}$ is the $(i, j)^{th}$ element of the precision matrix P. The partial correlations are performed for all patients and are then separated into two groups corresponding to patients with no evidence of disease and those patients in which CRC recurred. Probability distributions of the partial correlations—on the compact set [−1,1]—within each group are computed and the information distance between these two distributions is computed using the Jensen-Shannon divergence. This information distance defines the differential change in the association—partial correlation—between biomarkers $bm_i$ and $bm_j$ in the two patient cohorts. The greater the distance, the larger the differential change. Repeating this process for all N(N−1)/2 biomarker pairs results in the information distance matrices shown in FIGS. 15A-15C for the three spatial domains. These information distance matrices are thresholded at the $99^{th}$ percentile, resulting in the computationally inferred spatial-domain networks shown in FIGS. 15D-15F. The high percentile is chosen to ensure that most discriminative networks are captured.

Thus, as just described, the embodiment shown in FIG. 1 is a top-down strategy for implementing the disclosed concept that considers the combined effect of both biomarker intensity expressions and their related correlation features. This strategy is implemented via a modular approach that: (i) involves separate prediction modules for epithelial cells, stromal cells and epi-stroma interface cells to implicitly capture spatial context, (ii) performs penalized regression to identify the optimal and stable set of recurrence-associated features for each of the three modules, and (iii) integrates the resulting optimized modules into a joint multiplicative risk-model that predicts cancer recurrence risk.

In an alternative embodiment, the disclosed concept may also be implemented as a bottom-up strategy. In this alternative embodiment, after the spatial dissection and generation of the base feature set for each spatial domain is performed as described herein, univariate testing is performed wherein each feature in the base feature set for each spatial domain is tested independently for prognostic power in order to identify a salient subset of optimal features for the spatial domain. Once the subset of features for each spatial domain is determined, this alternative embodiment then proceeds to step 20 and 25 as described herein in order to generate a joint prognostic model for predicting cancer recurrence risk.

Figure 16:
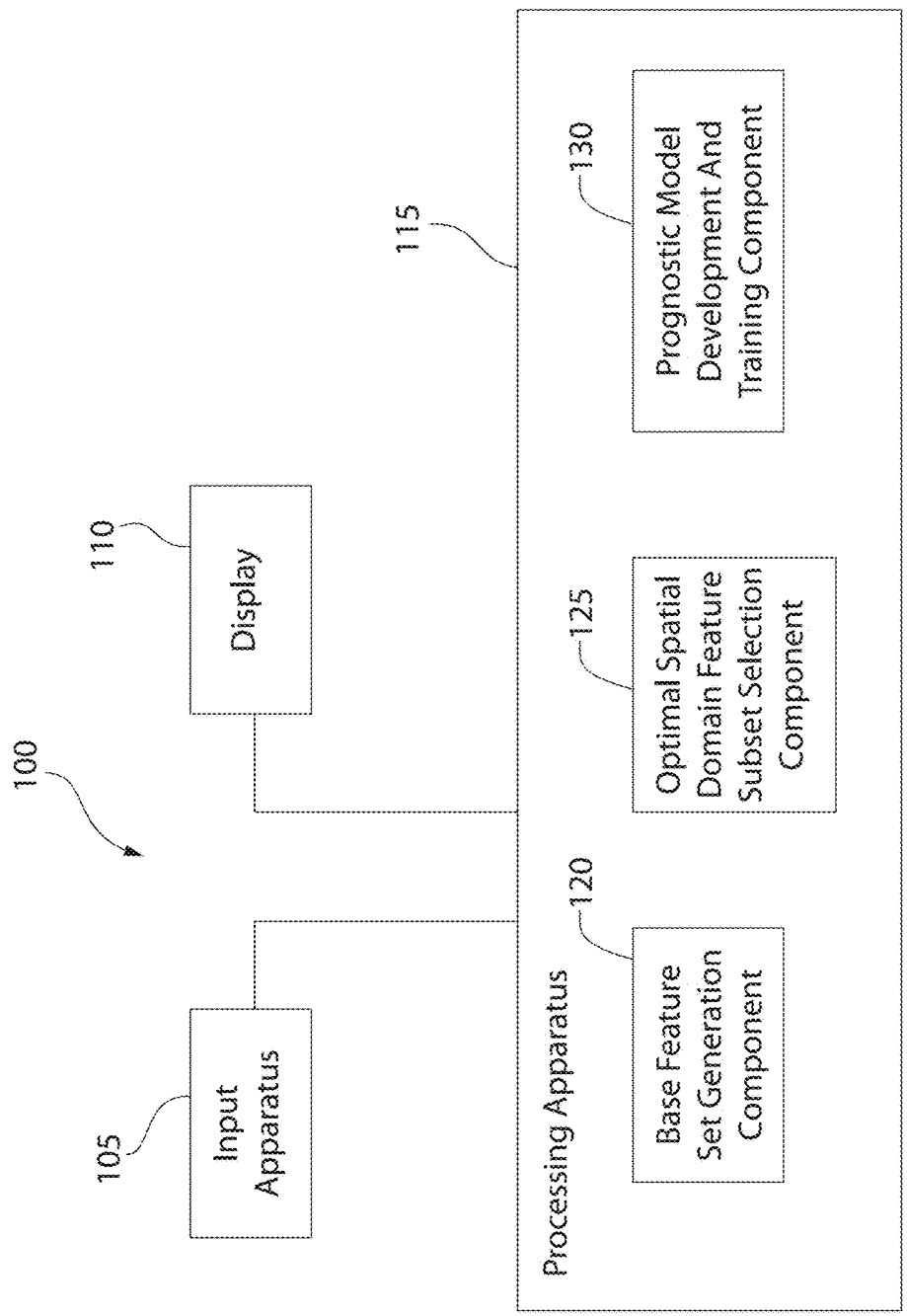
FIG. 16 is a schematic diagram of an exemplary system for developing and training a multivariate prognostic model for predicting cancer reoccurrence risk according to the disclosed concept.

FIG. 16 is a schematic diagram of an exemplary system 100 for developing and training a multivariate prognostic model for predicting cancer reoccurrence risk according to the disclosed concept as shown in FIG. 1 and described herein. As seen in FIG. 16, system 100 is a computing device structured and configured to generate/receive the multiplexed immunofluorescence biomarker data from tissue the cancer patient cohort as described herein and process that data as described herein to develop and train the spatial domain specific multivariate prognostic model. System 100 may be, for example and without limitation, a PC, a laptop computer, a tablet computer, or any other suitable device structured to perform the functionality described herein. System 100 includes an input apparatus 105 (such as a keyboard), a display 110 (such as an LCD), and a processing apparatus 115. A user is able to provide input into processing apparatus 115 using input apparatus 105, and processing apparatus 115 provides output signals to display 110 to enable display 110 to display information to the user as described in detail herein. Processing apparatus 115 comprises a processor and a memory. The processor may be, for example and without limitation, a microprocessor (μP), a microcontroller, or some other suitable processing device, that interfaces with the memory. The memory can be any one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. The memory has stored therein a number of routines that are executable by the processor, including routines for implementing the disclosed concept as described herein. In particular, processing apparatus 116 includes a base feature set generation component 120 configured for generating the base feature sets for each spatial from the multiplexed immunofluorescence biomarker data as described herein in the various embodiments, an optimal spatial domain feature subset selection component 125 configured for performing the testing and optimal feature subset selection as described herein in the various embodiments (e.g., via the top down or the bottom up strategy), and a prognostic model development and testing component configured for developing and training the joint multivariate prognostic model for predicting cancer reoccurrence risk as described herein in the various embodiments.

Figure 17:
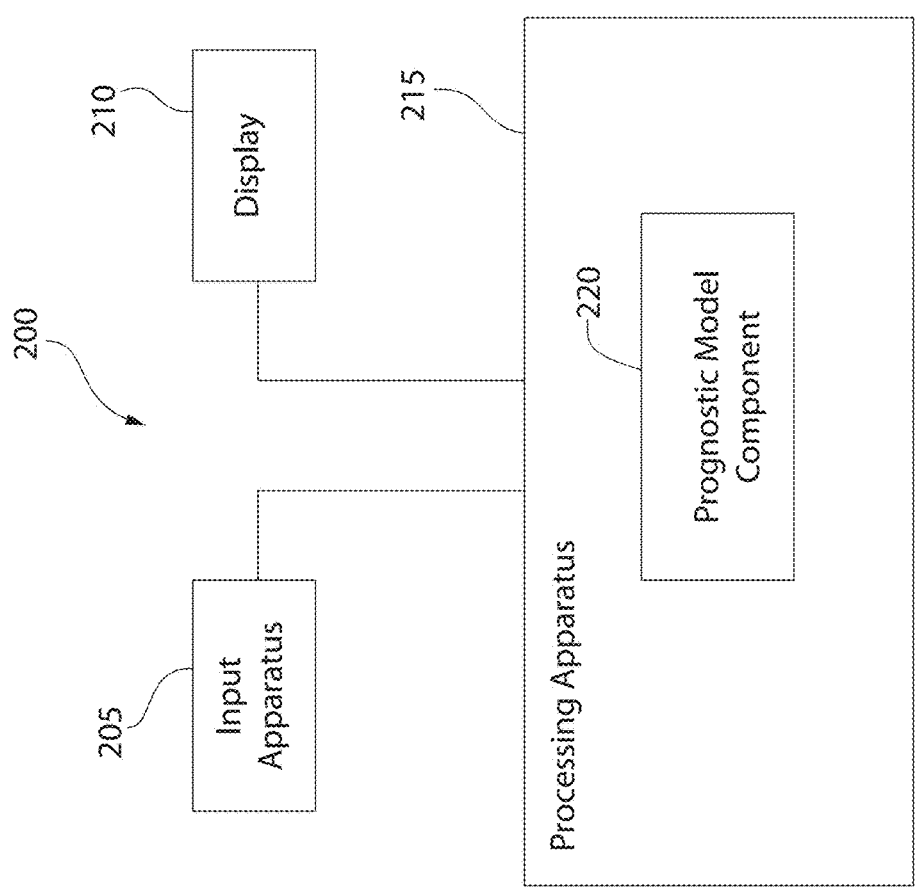
FIG. 17 is a schematic diagram of an exemplary digital pathology system in which the cancer recurrence risk prediction methodologies described herein may be implemented according one exemplary embodiment.

FIG. 17 is a schematic diagram of an exemplary digital pathology system 200 in which the cancer recurrence risk prediction methodologies described herein may be implemented according one exemplary embodiment. As seen in FIG. 17, system 200 is a computing device structured and configured to receive digital multiplexed immunofluorescence biomarker data for a tumor tissue sample of a patient and process that data as described herein to predict cancer reoccurrence risk for that patient based on and using the trained and tested multivariate prognostic model as described herein in its various embodiments. System 200 may be, for example and without limitation, a PC, a laptop computer, a tablet computer, a smartphone, or any other suitable device structured to perform the functionality described herein. System 200 includes an input apparatus 205 (such as a keyboard), a display 210 (such as an LCD), and a processing apparatus 215. A user is able to provide input into processing apparatus 215 using input apparatus 205, and processing apparatus 205 provides output signals to display 210 to enable display 210 to display information to the user as described in detail herein. Processing apparatus 215 comprises a processor and a memory. The processor may be, for example and without limitation, a microprocessor (RP), a microcontroller, or some other suitable processing device, that interfaces with the memory. The memory can be any one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. The memory has stored therein a number of routines that are executable by the processor, including routines for implementing the disclosed concept as described herein. In particular, processing apparatus 215 includes a prognostic model component that stores and implements the trained and tested joint multivariate prognostic model as described herein in its various embodiments (e.g., via the top down or the bottom up strategy). As a result, system 200 is able to receive digital multiplexed immunofluorescence biomarker data for a tumor tissue sample of a patient and process that data to predict cancer reoccurrence risk using the trained and tested multivariate prognostic model implemented in prognostic model component 220.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed:

1. A method of predicting cancer recurrence risk for an individual, comprising:
   receiving patient spatial multi-parameter cellular and sub-cellular imaging data labelled with a plurality of different biomarkers for a tumor of the individual;
   analyzing the patient spatial multi-parameter cellular and sub-cellular imaging data using a joint prognostic model for predicting cancer recurrence risk to determine a predicted cancer recurrence risk for the individual, wherein the joint prognostic model has been previously developed and trained by:
   receiving spatial multi-parameter cellular and sub-cellular imaging data labelled with the plurality of different biomarkers for a plurality of cancer patients, wherein the spatial multi-parameter cellular and sub-cellular imaging data for the plurality of cancer patients comprises multiplexed immunofluorescence biomarker data;
   performing a spatial dissection of the spatial multi-parameter cellular and sub-cellular imaging data for the plurality of cancer patients including cell segmentation to divide the multiplexed immunofluorescence biomarker data into a plurality of intra-tumor spatial domains;
   generating a base feature set for each of the intra-tumor spatial domains, wherein for each intra-tumor spatial domain the base feature set includes: (i) a computed intensity expression value for each of the plurality of different biomarkers, wherein the computed intensity expression value for each biomarker is a mean intensity value for the biomarker averaged across all cells within the intra-tumor spatial domain expressing the biomarker, and (ii) a plurality of Kendall rank correlation values, wherein each Kendall rank correlation value is between a respective pair of biomarkers of the plurality of different biomarkers for all cells within the intra-tumor spatial domain expressing the respective pair of biomarkers;
   for each of the intra-tumor spatial domains, determining an optimal subset of features from the base feature set for the intra-tumor spatial domain by testing each feature of the base feature set of the intra-tumor spatial domain using a regression method and determining those specific features from the base feature set that constitute the optimal subset;
   for each of the intra-tumor spatial domains, developing and training a spatial domain specific multivariate prognostic model for predicting cancer recurrence risk using the optimal subset of features of the intra-tumor spatial domain; and
   combining the spatial domain specific multivariate prognostic model of each of the intra-tumor spatial domains to form the joint prognostic model for predicting cancer recurrence risk.

2. The method according to claim 1, wherein the plurality of intra-tumor spatial domains comprise an epithelial spatial domain, a stromal spatial domain, and an epithelial-stromal domain.

3. The method according to claim 2, wherein the performing the spatial dissection comprises segmenting the spatial multi-parameter cellular and sub-cellular imaging data for the plurality of cancer patients into epithelial and stromal regions differentiated by epithelial E-cadherin staining.

4. The method according to claim 2, wherein the epithelial-stromal domain captures a boundary wherein stroma and malignant epithelial cells interact in close proximity.

5. The method according to claim 1, wherein, for each of the intra-tumor spatial domains, the selecting the subset of features from the base feature set for the intra-tumor spatial domain employs recurrence-guided learning.

6. The method according to claim 5, wherein, for each of the intra-tumor spatial domains, the selecting the subset of features from the base feature set for the intra-tumor spatial domain employs model selection based on an L1-penalized Cox proportional hazard regression method.

7. The method according to claim 6, wherein, for each of the intra-tumor spatial domains, the joint prognostic model has been previously developed and trained by learning coefficients for each feature in the subset of features using L2 penalty in a penalized Cox regression model with only the subset of features be used as inputs.

8. The method according to claim 7, wherein, for each of the intra-tumor spatial domains, the selecting the subset of features from the base feature set for the intra-tumor spatial domain further comprises testing for stability of contribution to recurrence prognosis through testing stability of the sign of each of the coefficients at a predetermined threshold.

9. The method according to claim 1, wherein, for each of the intra-tumor spatial domains, the selecting the subset of features from the base feature set for the intra-tumor spatial domain comprises testing the biomarkers used to generate the multiplexed immunofluorescence biomarker data together for prognostic power.

10. The method according to claim 1, wherein, for each of the intra-tumor spatial domains, the selecting the subset of features from the base feature set for the intra-tumor spatial domain comprises testing the biomarkers used to generate the multiplexed immunofluorescence biomarker data individually for prognostic power.

11. A computer program product, comprising a non-transitory computer usable medium having a computer readable program code embodied therein, the computer readable program code being adapted and configured to be executed to implement a method of predicting cancer recurrence risk for an individual as recited in claim 1, wherein the computer program product stores the joint prognostic model.

12. An apparatus for predicting cancer recurrence risk for an individual, comprising:
a computer system comprising a processing apparatus implementing a joint prognostic model for predicting cancer recurrence risk, wherein the processing apparatus is structured and configured to:
receive patient spatial multi-parameter cellular and sub-cellular imaging data labelled with a plurality of different biomarkers for a tumor of the individual; and
analyze the patient spatial multi-parameter cellular and sub-cellular imaging data using the joint prognostic model to determine a predicted cancer recurrence risk for the individual, wherein the joint prognostic model has been previously developed and trained by:
receiving spatial multi-parameter cellular and sub-cellular imaging data labelled with the plurality of different biomarkers for a plurality of cancer patients, wherein the spatial multi-parameter cellular and sub-cellular imaging data for the plurality of cancer patients comprises multiplexed immunofluorescence biomarker data;
performing a spatial dissection of the spatial multi-parameter cellular and sub-cellular imaging data for the plurality of cancer patients including cell segmentation to divide the multiplexed immunofluorescence biomarker data into a plurality of intra-tumor spatial domains;
generating a base feature set for each of the intra-tumor spatial domains, wherein for each intra-tumor spatial domain the base feature set includes: (i) a computed intensity expression value for each of the plurality of different biomarkers, wherein the computed intensity expression value for each biomarker is a mean intensity value for the biomarker averaged across all cells within the intra-tumor spatial domain expressing the biomarker, and (ii) a plurality of Kendall rank correlation values, wherein each Kendall rank correlation value is between a respective pair of biomarkers of the plurality of different biomarkers for all cells within the intra-tumor spatial domain expressing the respective pair of biomarkers;
for each of the intra-tumor spatial domains, determining an optimal subset of features from the base feature set for the intra-tumor spatial domain by testing each feature of the base feature set of the intra-tumor spatial domain using a regression method and determining those specific features from the base feature set that constitute the optimal subset;
for each of the intra-tumor spatial domains, developing and training a spatial domain specific multivariate prognostic model for predicting cancer recurrence risk using the optimal subset of features of the intra-tumor spatial domain; and
combining the spatial domain specific multivariate prognostic model of each of the intra-tumor spatial domains to form the joint prognostic model for predicting cancer recurrence risk.

13. The apparatus according to claim 12, wherein the plurality of intra-tumor spatial domains comprise an epithelial spatial domain, a stromal spatial domain, and a an epithelial-stromal domain.

14. The apparatus according to claim 13, wherein the performing the spatial dissection comprises segmenting the spatial multi-parameter cellular and sub-cellular imaging data for the plurality of cancer patients into epithelial and stromal regions differentiated by epithelial E-cadherin staining.

15. The apparatus according to claim 13, wherein the epithelial-stromal domain captures a boundary wherein stroma and malignant epithelial cells interact in close proximity.

16. The apparatus according to claim 12, wherein, for each of the intra-tumor spatial domains, the selecting the subset of features from the base feature set for the intra-tumor spatial domain employs recurrence-guided learning.

17. The apparatus according to claim 16, wherein, for each of the intra-tumor spatial domains, the selecting the subset of features from the base feature set for the intra-tumor spatial domain employs model selection based on an L1-penalized Cox proportional hazard regression method.

18. The apparatus according to claim 17, wherein, for each of the intra-tumor spatial domains, the joint prognostic model has been previously developed and trained by learning coefficients for each feature in the subset of features using L2 penalty in a penalized Cox regression model with only the subset of features be used as inputs.

19. The apparatus according to claim 18, wherein, for each of the intra-tumor spatial domains, the selecting the subset of features from the base feature set for the intra-tumor spatial domain further comprises testing for stability of contribution to recurrence prognosis through testing stability of the sign of each of the coefficients at a predetermined threshold.

20. The apparatus according to claim 12, wherein, for each of the intra-tumor spatial domains, the selecting the subset of features from the base feature set for the intra-tumor spatial domain comprises testing the biomarkers used to generate the multiplexed immunofluorescence biomarker data together for prognostic power.

21. The apparatus according to claim 12, wherein, for each of the intra-tumor spatial domains, the selecting the subset of features from the base feature set for the intra-tumor spatial domain comprises testing the biomarkers used to generate the multiplexed immunofluorescence biomarker data individually for prognostic power.

22. A method of creating a joint prognostic model for predicting cancer recurrence risk, comprising:
- receiving spatial multi-parameter cellular and sub-cellular imaging data labelled with a plurality of different biomarkers for a plurality of cancer patients, wherein the spatial multi-parameter cellular and sub-cellular imaging data for the plurality of cancer patients comprises multiplexed immunofluorescence biomarker data;
- performing spatial dissection including cell segmentation on the multiplexed immunofluorescence biomarker data to divide the multiplexed immunofluorescence biomarker imaging data into a plurality of intra-tumor spatial domains;
- generating a base feature set for each of the intra-tumor spatial domains, wherein for each intra-tumor spatial domain the base feature set includes: (i) a computed intensity expression value for each of the plurality of different biomarkers, wherein the computed intensity expression value for each biomarker is a mean intensity value for the biomarker averaged across all cells within the intra-tumor spatial domain expressing the biomarker, and (ii) a plurality of Kendall rank correlation values, wherein each Kendall rank correlation value is between a respective pair of biomarkers of the plurality of different biomarkers for all cells within the intra-tumor spatial domain expressing the respective pair of biomarkers;
- for each of the intra-tumor spatial domains, determining an optimal subset of features from the base feature set for the intra-tumor spatial domain by testing each feature of the base feature set of the intra-tumor spatial domain using a regression method and determining those specific features from the base feature set that constitute the optimal subset;
- for each of the intra-tumor spatial domains, developing and training a spatial domain specific multivariate prognostic model for predicting cancer recurrence risk using the optimal subset of features of the intra-tumor spatial domain;
- combining the spatial domain specific multivariate prognostic model of each of the intra-tumor spatial domains to form the joint prognostic model for predicting cancer recurrence risk.

* * * * *